(12) United States Patent
Magro

(10) Patent No.: US 8,999,340 B2
(45) Date of Patent: Apr. 7, 2015

(54) METHODS FOR TREATING MULTIORGAN, SYSTEMIC DEGOS' DISEASE WITH A COMPLEMENT INHIBITOR

(75) Inventor: Cynthia Magro, New York, NY (US)

(73) Assignee: Alexion Pharmaceuticals, Inc., Cheshire, CT (US)

(*) Notice: Subject to any disclaimer, the term of this patent is extended or adjusted under 35 U.S.C. 154(b) by 0 days.

(21) Appl. No.: 13/582,018

(22) PCT Filed: Mar. 1, 2011

(86) PCT No.: PCT/US2011/026602
§ 371 (c)(1),
(2), (4) Date: Nov. 16, 2012

(87) PCT Pub. No.: WO2011/109338
PCT Pub. Date: Sep. 9, 2011

(65) Prior Publication Data
US 2013/0064820 A1 Mar. 14, 2013

Related U.S. Application Data

(60) Provisional application No. 61/309,393, filed on Mar. 1, 2010.

(51) Int. Cl.
| | |
|---|---|
| A61K 39/395 | (2006.01) |
| C07K 14/00 | (2006.01) |
| A61K 38/17 | (2006.01) |
| A61K 31/245 | (2006.01) |
| A61K 38/12 | (2006.01) |
| A61K 45/06 | (2006.01) |
| C07K 16/18 | (2006.01) |

(52) U.S. Cl.
CPC ........... *A61K 38/1725* (2013.01); *A61K 31/245* (2013.01); *A61K 38/12* (2013.01); *A61K 45/06* (2013.01); *C07K 16/18* (2013.01); *C07K 2317/24* (2013.01); *C07K 2317/76* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 2009/0148462 A1* | 6/2009 | Chevrier et al. | 424/158.1 |
| 2011/0002931 A1 | 1/2011 | Tamburini | |
| 2011/0046094 A1* | 2/2011 | Behrens et al. | 514/169 |
| 2012/0225056 A1* | 9/2012 | Rother et al. | 424/133.1 |

FOREIGN PATENT DOCUMENTS

| | | |
|---|---|---|
| CN | 102271703 | 12/2011 |
| WO | WO 2009/149306 A9 | 12/2009 |
| WO | WO 2010/054403 A1 | 5/2010 |
| WO | 2010/151526 A1 | 12/2010 |

OTHER PUBLICATIONS

Written Opinion of the International Searching Authority of the corresponding PCT/US2011/026602 (Sep. 1, 2012).*
Attwood, Science 290: 471-473, 2000.*
Skolnick et al., Trends in Biotech. 18: 34-39, 2000.*
Ricklin et al., Nature Biotechnology 25: 1265-1275, 2007.*
Ball, E., et al., "Degas' Disease: A Distinctive Pattern of Disease, Chiefly of Lupus Erythematosus, And Not a Specific Disease per se," The American Journal of Dermatopathology, 25(4):308-320 (2003).
Garrett-Bakelman, F., et al., "C5B-9 is a Potential Effector in the Pathophysiology of Degos Disease; a Case Report of Treatment with Eculizumab," XXXIII World Congress of the International Society of Hematology, Oct. 10-13, 2010, Abstract. [retrieved on May 4, 2011]. Retrieved from the Internet www.kenes.com/ish2010/abstracts/Authors.htm.
High, W.A., et al., "Is Degas' Disease a Clinical Histological End Point Rather Than a Specific Disease?" Journal of the American Academy of Dermatology, 50:895-899 (2004).
Magro, C.M., et al., "Fulminant and Accelerated Presentation of Dermatomyositis in Two Previously Healthy Young Adult Males: A Potential Role for Endotheliotropic Viral Infection," Journal of Cutaneous Pathology, 36:853-858 (2009).
Molenaar, W.M., et al., "The Pathology and Pathogenesis of Malignant Atrophic Papulosis (Degos' Disease)—A Case Study with Reference to Other Vascular Disorders," Pathology Research and Practice, 182:98-106 (1987).
Rather, R.P., et al., "Inhibition of Terminal Complement: A Novel Therapeutic Approach for the Treatment of Systemic Lupus Erythematosus," Lupus, 13:328-334 (2004).
Scheinfeld, N.S., "Degos Disease Treatment & Management" updated Aug. 16, 2010 [retrieved on May 4, 2011]. Retrieved from the Internet. ://emedicine.medscape.com/article/1087180-tratment.
Wagner, E., and Frank, M.M., "Therapeutic Potential of Complement Modulation," Nature Reviews; Drug Discovery, 9:43-56 (Jan. 2010).
Magro et al., "Degos Disease A C5b-9/lnterferon-alpha-Mediated Endotheliopathy Syndrome," American Journal of Clinical Pathology, vol. 135(4): 599-610 (2011).
Supplementary European Search Report for EP 11 75 1164, dated Jul. 2, 2013.
Fernandez-Flores, A. et al., "Diabetes mellitus and Degos disease," Bratisl Lek Listy, vol. 109(9):414-417 (2008).

\* cited by examiner

*Primary Examiner* — Phillip Gambel
(74) *Attorney, Agent, or Firm* — Nelson Mullins Riley & Scarborough LLP; Jane E. Remillard, Esq.; Jill Gorney Sloper, Esq.

(57) ABSTRACT

The present disclosure relates to, inter alia, compositions containing an inhibitor of human complement and/or an inhibitor of interferon alpha, and the use of the compositions in methods for treating or preventing Degos' disease in a subject. In some embodiments, the inhibitor is an antibody, or antigen-binding fragment thereof, that binds to a human complement component C5 protein or to a biologically-active fragment of C5 such as C5a or C5b. In some embodiments, the inhibitor is an antibody, or an antigen-binding fragment thereof, that binds to interferon alpha or to an interferon alpha receptor.

18 Claims, No Drawings

SEQUENCE LISTING

```
<160> NUMBER OF SEQ ID NOS: 26

<210> SEQ ID NO 1
<211> LENGTH: 1676
<212> TYPE: PRT
<213> ORGANISM: Homo sapiens

<400> SEQUENCE: 1

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175
```

```
Ile Asp His Ile Gly Ile Ile Ser Phe Pro Asp Phe Lys Ile Pro Ser
            180                 185                 190
Asn Pro Arg Tyr Gly Met Trp Thr Ile Lys Ala Lys Tyr Lys Glu Asp
            195                 200                 205
Phe Ser Thr Thr Gly Thr Ala Tyr Phe Glu Val Lys Glu Tyr Val Leu
            210                 215                 220
Pro His Phe Ser Val Ser Ile Glu Pro Glu Tyr Asn Phe Ile Gly Tyr
225                 230                 235                 240
Lys Asn Phe Lys Asn Phe Glu Ile Thr Ile Lys Ala Arg Tyr Phe Tyr
                245                 250                 255
Asn Lys Val Val Thr Glu Ala Asp Val Tyr Ile Thr Phe Gly Ile Arg
            260                 265                 270
Glu Asp Leu Lys Asp Asp Gln Lys Glu Met Met Gln Thr Ala Met Gln
            275                 280                 285
Asn Thr Met Leu Ile Asn Gly Ile Ala Gln Val Thr Phe Asp Ser Glu
            290                 295                 300
Thr Ala Val Lys Glu Leu Ser Tyr Tyr Ser Leu Glu Asp Leu Asn Asn
305                 310                 315                 320
Lys Tyr Leu Tyr Ile Ala Val Thr Val Ile Glu Ser Thr Gly Gly Phe
                325                 330                 335
Ser Glu Glu Ala Glu Ile Pro Gly Ile Lys Tyr Val Leu Ser Pro Tyr
            340                 345                 350
Lys Leu Asn Leu Val Ala Thr Pro Leu Phe Leu Lys Pro Gly Ile Pro
            355                 360                 365
Tyr Pro Ile Lys Val Gln Val Lys Asp Ser Leu Asp Gln Leu Val Gly
            370                 375                 380
Gly Val Pro Val Ile Leu Asn Ala Gln Thr Ile Asp Val Asn Gln Glu
385                 390                 395                 400
Thr Ser Asp Leu Asp Pro Ser Lys Ser Val Thr Arg Val Asp Asp Gly
            405                 410                 415
Val Ala Ser Phe Val Leu Asn Leu Pro Ser Gly Val Thr Val Leu Glu
            420                 425                 430
Phe Asn Val Lys Thr Asp Ala Pro Asp Leu Pro Glu Glu Asn Gln Ala
            435                 440                 445
Arg Glu Gly Tyr Arg Ala Ile Ala Tyr Ser Ser Leu Ser Gln Ser Tyr
            450                 455                 460
Leu Tyr Ile Asp Trp Thr Asp Asn His Lys Ala Leu Leu Val Gly Glu
465                 470                 475                 480
His Leu Asn Ile Ile Val Thr Pro Lys Ser Pro Tyr Ile Asp Lys Ile
                485                 490                 495
Thr His Tyr Asn Tyr Leu Ile Leu Ser Lys Gly Lys Ile His Phe
            500                 505                 510
Gly Thr Arg Glu Lys Phe Ser Asp Ala Ser Tyr Gln Ser Ile Asn Ile
            515                 520                 525
Pro Val Thr Gln Asn Met Val Pro Ser Ser Arg Leu Leu Val Tyr Tyr
            530                 535                 540
Ile Val Thr Gly Glu Gln Thr Ala Glu Leu Val Ser Asp Ser Val Trp
545                 550                 555                 560
Leu Asn Ile Glu Glu Lys Cys Gly Asn Gln Leu Gln Val His Leu Ser
                565                 570                 575
Pro Asp Ala Asp Ala Tyr Ser Pro Gly Gln Thr Val Ser Leu Asn Met
            580                 585                 590
```

```
Ala Thr Gly Met Asp Ser Trp Val Ala Leu Ala Ala Val Asp Ser Ala
            595                 600                 605

Val Tyr Gly Val Gln Arg Gly Ala Lys Lys Pro Leu Glu Arg Val Phe
    610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu Arg Pro Arg Arg Thr Leu Gln Lys Lys Ile Glu Glu Ile Ala Ala
        675                 680                 685

Lys Tyr Lys His Ser Val Val Lys Cys Cys Tyr Asp Gly Ala Cys
690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
        740                 745                 750

His Met Lys Thr Leu Leu Pro Val Ser Lys Pro Glu Ile Arg Ser Tyr
    755                 760                 765

Phe Pro Glu Ser Trp Leu Trp Glu Val His Leu Val Pro Arg Arg Lys
770                 775                 780

Gln Leu Gln Phe Ala Leu Pro Asp Ser Leu Thr Thr Trp Glu Ile Gln
785                 790                 795                 800

Gly Ile Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
        835                 840                 845

Arg Thr Ser Gly Met Gln Phe Cys Val Lys Met Ser Ala Val Glu Gly
    850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
        915                 920                 925

Val Val Pro Glu Gly Val Lys Arg Glu Ser Tyr Ser Gly Val Thr Leu
    930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Gln Glu Gly Ile Asn Ile Leu Thr His Leu Pro Lys Gly Ser Ala
        995                 1000                1005

Glu Ala Glu Leu Met Ser Val Val Pro Val Phe Tyr Val Phe His
```

```
            1010                1015                1020

Tyr Leu Glu Thr Gly Asn His Trp Asn Ile Phe His Ser Asp Pro
            1025                1030                1035

Leu Ile Glu Lys Gln Lys Leu Lys Lys Lys Leu Lys Glu Gly Met
            1040                1045                1050

Leu Ser Ile Met Ser Tyr Arg Asn Ala Asp Tyr Ser Tyr Ser Val
            1055                1060                1065

Trp Lys Gly Gly Ser Ala Ser Thr Trp Leu Thr Ala Phe Ala Leu
            1070                1075                1080

Arg Val Leu Gly Gln Val Asn Lys Tyr Val Glu Gln Asn Gln Asn
            1085                1090                1095

Ser Ile Cys Asn Ser Leu Leu Trp Leu Val Glu Asn Tyr Gln Leu
            1100                1105                1110

Asp Asn Gly Ser Phe Lys Glu Asn Ser Gln Tyr Gln Pro Ile Lys
            1115                1120                1125

Leu Gln Gly Thr Leu Pro Val Glu Ala Arg Glu Asn Ser Leu Tyr
            1130                1135                1140

Leu Thr Ala Phe Thr Val Ile Gly Ile Arg Lys Ala Phe Asp Ile
            1145                1150                1155

Cys Pro Leu Val Lys Ile Asp Thr Ala Leu Ile Lys Ala Asp Asn
            1160                1165                1170

Phe Leu Leu Glu Asn Thr Leu Pro Ala Gln Ser Thr Phe Thr Leu
            1175                1180                1185

Ala Ile Ser Ala Tyr Ala Leu Ser Leu Gly Asp Lys Thr His Pro
            1190                1195                1200

Gln Phe Arg Ser Ile Val Ser Ala Leu Lys Arg Glu Ala Leu Val
            1205                1210                1215

Lys Gly Asn Pro Pro Ile Tyr Arg Phe Trp Lys Asp Asn Leu Gln
            1220                1225                1230

His Lys Asp Ser Ser Val Pro Asn Thr Gly Thr Ala Arg Met Val
            1235                1240                1245

Glu Thr Thr Ala Tyr Ala Leu Leu Thr Ser Leu Asn Leu Lys Asp
            1250                1255                1260

Ile Asn Tyr Val Asn Pro Val Ile Lys Trp Leu Ser Glu Glu Gln
            1265                1270                1275

Arg Tyr Gly Gly Gly Phe Tyr Ser Thr Gln Asp Thr Ile Asn Ala
            1280                1285                1290

Ile Glu Gly Leu Thr Glu Tyr Ser Leu Leu Val Lys Gln Leu Arg
            1295                1300                1305

Leu Ser Met Asp Ile Asp Val Ser Tyr Lys His Lys Gly Ala Leu
            1310                1315                1320

His Asn Tyr Lys Met Thr Asp Lys Asn Phe Leu Gly Arg Pro Val
            1325                1330                1335

Glu Val Leu Leu Asn Asp Asp Leu Ile Val Ser Thr Gly Phe Gly
            1340                1345                1350

Ser Gly Leu Ala Thr Val His Val Thr Thr Val Val His Lys Thr
            1355                1360                1365

Ser Thr Ser Glu Glu Val Cys Ser Phe Tyr Leu Lys Ile Asp Thr
            1370                1375                1380

Gln Asp Ile Glu Ala Ser His Tyr Arg Gly Tyr Gly Asn Ser Asp
            1385                1390                1395

Tyr Lys Arg Ile Val Ala Cys Ala Ser Tyr Lys Pro Ser Arg Glu
            1400                1405                1410
```

Glu Ser Ser Ser Gly Ser Ser His Ala Val Met Asp Ile Ser Leu
    1415                1420                1425

Pro Thr Gly Ile Ser Ala Asn Glu Glu Asp Leu Lys Ala Leu Val
    1430                1435                1440

Glu Gly Val Asp Gln Leu Phe Thr Asp Tyr Gln Ile Lys Asp Gly
    1445                1450                1455

His Val Ile Leu Gln Leu Asn Ser Ile Pro Ser Ser Asp Phe Leu
    1460                1465                1470

Cys Val Arg Phe Arg Ile Phe Glu Leu Phe Glu Val Gly Phe Leu
    1475                1480                1485

Ser Pro Ala Thr Phe Thr Val Tyr Glu Tyr His Arg Pro Asp Lys
    1490                1495                1500

Gln Cys Thr Met Phe Tyr Ser Thr Ser Asn Ile Lys Ile Gln Lys
    1505                1510                1515

Val Cys Glu Gly Ala Ala Cys Lys Cys Val Glu Ala Asp Cys Gly
    1520                1525                1530

Gln Met Gln Glu Glu Leu Asp Leu Thr Ile Ser Ala Glu Thr Arg
    1535                1540                1545

Lys Gln Thr Ala Cys Lys Pro Glu Ile Ala Tyr Ala Tyr Lys Val
    1550                1555                1560

Ser Ile Thr Ser Ile Thr Val Glu Asn Val Phe Val Lys Tyr Lys
    1565                1570                1575

Ala Thr Leu Leu Asp Ile Tyr Lys Thr Gly Glu Ala Val Ala Glu
    1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 2
<211> LENGTH: 1658
<212> TYPE: PRT
<213> ORGANISM: Homo sapiens

<400> SEQUENCE: 2

Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
                20                  25                  30

Asp Ala Thr Ile Ser Ile Lys Ser Tyr Pro Asp Lys Lys Phe Ser Tyr
            35                  40                  45

Ser Ser Gly His Val His Leu Ser Ser Glu Asn Lys Phe Gln Asn Ser
        50                  55                  60

Ala Ile Leu Thr Ile Gln Pro Lys Gln Leu Pro Gly Gly Gln Asn Pro
65                  70                  75                  80

Val Ser Tyr Val Tyr Leu Glu Val Val Ser Lys His Phe Ser Lys Ser

```
            85                  90                  95
Lys Arg Met Pro Ile Thr Tyr Asp Asn Gly Phe Leu Phe Ile His Thr
            100                 105                 110

Asp Lys Pro Val Tyr Thr Pro Asp Gln Ser Val Lys Val Arg Val Tyr
            115                 120                 125

Ser Leu Asn Asp Asp Leu Lys Pro Ala Lys Arg Glu Thr Val Leu Thr
            130                 135                 140

Phe Ile Asp Pro Glu Gly Ser Glu Val Asp Met Val Glu Glu Ile Asp
145                 150                 155                 160

His Ile Gly Ile Ile Ser Phe Pro Asp Phe Lys Ile Pro Ser Asn Pro
                    165                 170                 175

Arg Tyr Gly Met Trp Thr Ile Lys Ala Lys Tyr Lys Glu Asp Phe Ser
                    180                 185                 190

Thr Thr Gly Thr Ala Tyr Phe Glu Val Lys Glu Tyr Val Leu Pro His
                    195                 200                 205

Phe Ser Val Ser Ile Glu Pro Glu Tyr Asn Phe Ile Gly Tyr Lys Asn
            210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                    245                 250                 255

Leu Lys Asp Asp Gln Lys Glu Met Met Gln Thr Ala Met Gln Asn Thr
            260                 265                 270

Met Leu Ile Asn Gly Ile Ala Gln Val Thr Phe Asp Ser Glu Thr Ala
            275                 280                 285

Val Lys Glu Leu Ser Tyr Tyr Ser Leu Glu Asp Leu Asn Asn Lys Tyr
            290                 295                 300

Leu Tyr Ile Ala Val Thr Val Ile Glu Ser Thr Gly Gly Phe Ser Glu
305                 310                 315                 320

Glu Ala Glu Ile Pro Gly Ile Lys Tyr Val Leu Ser Pro Tyr Lys Leu
                    325                 330                 335

Asn Leu Val Ala Thr Pro Leu Phe Leu Lys Pro Gly Ile Pro Tyr Pro
            340                 345                 350

Ile Lys Val Gln Val Lys Asp Ser Leu Asp Gln Leu Val Gly Gly Val
            355                 360                 365

Pro Val Ile Leu Asn Ala Gln Thr Ile Asp Val Asn Gln Glu Thr Ser
            370                 375                 380

Asp Leu Asp Pro Ser Lys Ser Val Thr Arg Val Asp Asp Gly Val Ala
385                 390                 395                 400

Ser Phe Val Leu Asn Leu Pro Ser Gly Val Thr Val Leu Glu Phe Asn
                    405                 410                 415

Val Lys Thr Asp Ala Pro Asp Leu Pro Glu Glu Asn Gln Ala Arg Glu
            420                 425                 430

Gly Tyr Arg Ala Ile Ala Tyr Ser Ser Leu Ser Gln Ser Tyr Leu Tyr
            435                 440                 445

Ile Asp Trp Thr Asp Asn His Lys Ala Leu Leu Val Gly Glu His Leu
            450                 455                 460

Asn Ile Ile Val Thr Pro Lys Ser Pro Tyr Ile Asp Lys Ile Thr His
465                 470                 475                 480

Tyr Asn Tyr Leu Ile Leu Ser Lys Gly Lys Ile Ile His Phe Gly Thr
                    485                 490                 495

Arg Glu Lys Phe Ser Asp Ala Ser Tyr Gln Ser Ile Asn Ile Pro Val
            500                 505                 510
```

```
Thr Gln Asn Met Val Pro Ser Ser Arg Leu Leu Val Tyr Tyr Ile Val
            515                 520                 525
Thr Gly Glu Gln Thr Ala Glu Leu Val Ser Asp Ser Val Trp Leu Asn
        530                 535                 540
Ile Glu Glu Lys Cys Gly Asn Gln Leu Gln Val His Leu Ser Pro Asp
545                 550                 555                 560
Ala Asp Ala Tyr Ser Pro Gly Gln Thr Val Ser Leu Asn Met Ala Thr
                565                 570                 575
Gly Met Asp Ser Trp Val Ala Leu Ala Ala Val Asp Ser Ala Val Tyr
            580                 585                 590
Gly Val Gln Arg Gly Ala Lys Lys Pro Leu Glu Arg Val Phe Gln Phe
        595                 600                 605
Leu Glu Lys Ser Asp Leu Gly Cys Gly Ala Gly Gly Gly Leu Asn Asn
    610                 615                 620
Ala Asn Val Phe His Leu Ala Gly Leu Thr Phe Leu Thr Asn Ala Asn
625                 630                 635                 640
Ala Asp Asp Ser Gln Glu Asn Asp Glu Pro Cys Lys Glu Ile Leu Arg
                645                 650                 655
Pro Arg Arg Thr Leu Gln Lys Lys Ile Glu Glu Ile Ala Ala Lys Tyr
            660                 665                 670
Lys His Ser Val Val Lys Lys Cys Cys Tyr Asp Gly Ala Cys Val Asn
        675                 680                 685
Asn Asp Glu Thr Cys Glu Gln Arg Ala Ala Arg Ile Ser Leu Gly Pro
    690                 695                 700
Arg Cys Ile Lys Ala Phe Thr Glu Cys Cys Val Val Ala Ser Gln Leu
705                 710                 715                 720
Arg Ala Asn Ile Ser His Lys Asp Met Gln Leu Gly Arg Leu His Met
                725                 730                 735
Lys Thr Leu Leu Pro Val Ser Lys Pro Glu Ile Arg Ser Tyr Phe Pro
            740                 745                 750
Glu Ser Trp Leu Trp Glu Val His Leu Val Pro Arg Arg Lys Gln Leu
        755                 760                 765
Gln Phe Ala Leu Pro Asp Ser Leu Thr Thr Trp Glu Ile Gln Gly Ile
    770                 775                 780
Gly Ile Ser Asn Thr Gly Ile Cys Val Ala Asp Thr Val Lys Ala Lys
785                 790                 795                 800
Val Phe Lys Asp Val Phe Leu Glu Met Asn Ile Pro Tyr Ser Val Val
                805                 810                 815
Arg Gly Glu Gln Ile Gln Leu Lys Gly Thr Val Tyr Asn Tyr Arg Thr
            820                 825                 830
Ser Gly Met Gln Phe Cys Val Lys Met Ser Ala Val Glu Gly Ile Cys
        835                 840                 845
Thr Ser Glu Ser Pro Val Ile Asp His Gln Gly Thr Lys Ser Ser Lys
    850                 855                 860
Cys Val Arg Gln Lys Val Glu Gly Ser Ser His Leu Val Thr Phe
865                 870                 875                 880
Thr Val Leu Pro Leu Glu Ile Gly Leu His Asn Ile Asn Phe Ser Leu
                885                 890                 895
Glu Thr Trp Phe Gly Lys Glu Ile Leu Val Lys Thr Leu Arg Val Val
            900                 905                 910
Pro Glu Gly Val Lys Arg Glu Ser Tyr Ser Gly Val Thr Leu Asp Pro
        915                 920                 925
```

```
Arg Gly Ile Tyr Gly Thr Ile Ser Arg Arg Lys Glu Phe Pro Tyr Arg
930                 935                 940

Ile Pro Leu Asp Leu Val Pro Lys Thr Glu Ile Lys Arg Ile Leu Ser
945                 950                 955                 960

Val Lys Gly Leu Leu Val Gly Glu Ile Leu Ser Ala Val Leu Ser Gln
                965                 970                 975

Glu Gly Ile Asn Ile Leu Thr His Leu Pro Lys Gly Ser Ala Glu Ala
                980                 985                 990

Glu Leu Met Ser Val Val Pro Val Phe Tyr Val Phe His Tyr Leu Glu
            995                 1000                1005

Thr Gly Asn His Trp Asn Ile Phe His Ser Asp Pro Leu Ile Glu
    1010                1015                1020

Lys Gln Lys Leu Lys Lys Lys Leu Lys Glu Gly Met Leu Ser Ile
    1025                1030                1035

Met Ser Tyr Arg Asn Ala Asp Tyr Ser Tyr Ser Val Trp Lys Gly
    1040                1045                1050

Gly Ser Ala Ser Thr Trp Leu Thr Ala Phe Ala Leu Arg Val Leu
    1055                1060                1065

Gly Gln Val Asn Lys Tyr Val Glu Gln Asn Gln Asn Ser Ile Cys
    1070                1075                1080

Asn Ser Leu Leu Trp Leu Val Glu Asn Tyr Gln Leu Asp Asn Gly
    1085                1090                1095

Ser Phe Lys Glu Asn Ser Gln Tyr Gln Pro Ile Lys Leu Gln Gly
    1100                1105                1110

Thr Leu Pro Val Glu Ala Arg Glu Asn Ser Leu Tyr Leu Thr Ala
    1115                1120                1125

Phe Thr Val Ile Gly Ile Arg Lys Ala Phe Asp Ile Cys Pro Leu
    1130                1135                1140

Val Lys Ile Asp Thr Ala Leu Ile Lys Ala Asp Asn Phe Leu Leu
    1145                1150                1155

Glu Asn Thr Leu Pro Ala Gln Ser Thr Phe Thr Leu Ala Ile Ser
    1160                1165                1170

Ala Tyr Ala Leu Ser Leu Gly Asp Lys Thr His Pro Gln Phe Arg
    1175                1180                1185

Ser Ile Val Ser Ala Leu Lys Arg Glu Ala Leu Val Lys Gly Asn
    1190                1195                1200

Pro Pro Ile Tyr Arg Phe Trp Lys Asp Asn Leu Gln His Lys Asp
    1205                1210                1215

Ser Ser Val Pro Asn Thr Gly Thr Ala Arg Met Val Glu Thr Thr
    1220                1225                1230

Ala Tyr Ala Leu Leu Thr Ser Leu Asn Leu Lys Asp Ile Asn Tyr
    1235                1240                1245

Val Asn Pro Val Ile Lys Trp Leu Ser Glu Glu Gln Arg Tyr Gly
    1250                1255                1260

Gly Gly Phe Tyr Ser Thr Gln Asp Thr Ile Asn Ala Ile Glu Gly
    1265                1270                1275

Leu Thr Glu Tyr Ser Leu Leu Val Lys Gln Leu Arg Leu Ser Met
    1280                1285                1290

Asp Ile Asp Val Ser Tyr Lys His Lys Gly Ala Leu His Asn Tyr
    1295                1300                1305

Lys Met Thr Asp Lys Asn Phe Leu Gly Arg Pro Val Glu Val Leu
    1310                1315                1320

Leu Asn Asp Asp Leu Ile Val Ser Thr Gly Phe Gly Ser Gly Leu
```

```
            1325                1330                1335

Ala  Thr  Val  His  Val  Thr  Thr  Val  Val  His  Lys  Thr  Ser  Thr  Ser
       1340                1345                1350

Glu  Glu  Val  Cys  Ser  Phe  Tyr  Leu  Lys  Ile  Asp  Thr  Gln  Asp  Ile
       1355                1360                1365

Glu  Ala  Ser  His  Tyr  Arg  Gly  Tyr  Gly  Asn  Ser  Asp  Tyr  Lys  Arg
       1370                1375                1380

Ile  Val  Ala  Cys  Ala  Ser  Tyr  Lys  Pro  Ser  Arg  Glu  Glu  Ser  Ser
       1385                1390                1395

Ser  Gly  Ser  Ser  His  Ala  Val  Met  Asp  Ile  Ser  Leu  Pro  Thr  Gly
       1400                1405                1410

Ile  Ser  Ala  Asn  Glu  Glu  Asp  Leu  Lys  Ala  Leu  Val  Glu  Gly  Val
       1415                1420                1425

Asp  Gln  Leu  Phe  Thr  Asp  Tyr  Gln  Ile  Lys  Asp  Gly  His  Val  Ile
       1430                1435                1440

Leu  Gln  Leu  Asn  Ser  Ile  Pro  Ser  Ser  Asp  Phe  Leu  Cys  Val  Arg
       1445                1450                1455

Phe  Arg  Ile  Phe  Glu  Leu  Phe  Glu  Val  Gly  Phe  Leu  Ser  Pro  Ala
       1460                1465                1470

Thr  Phe  Thr  Val  Tyr  Glu  Tyr  His  Arg  Pro  Asp  Lys  Gln  Cys  Thr
       1475                1480                1485

Met  Phe  Tyr  Ser  Thr  Ser  Asn  Ile  Lys  Ile  Gln  Lys  Val  Cys  Glu
       1490                1495                1500

Gly  Ala  Ala  Cys  Lys  Cys  Val  Glu  Ala  Asp  Cys  Gly  Gln  Met  Gln
       1505                1510                1515

Glu  Glu  Leu  Asp  Leu  Thr  Ile  Ser  Ala  Glu  Thr  Arg  Lys  Gln  Thr
       1520                1525                1530

Ala  Cys  Lys  Pro  Glu  Ile  Ala  Tyr  Ala  Tyr  Lys  Val  Ser  Ile  Thr
       1535                1540                1545

Ser  Ile  Thr  Val  Glu  Asn  Val  Phe  Val  Lys  Tyr  Lys  Ala  Thr  Leu
       1550                1555                1560

Leu  Asp  Ile  Tyr  Lys  Thr  Gly  Glu  Ala  Val  Ala  Glu  Lys  Asp  Ser
       1565                1570                1575

Glu  Ile  Thr  Phe  Ile  Lys  Lys  Val  Thr  Cys  Thr  Asn  Ala  Glu  Leu
       1580                1585                1590

Val  Lys  Gly  Arg  Gln  Tyr  Leu  Ile  Met  Gly  Lys  Glu  Ala  Leu  Gln
       1595                1600                1605

Ile  Lys  Tyr  Asn  Phe  Ser  Phe  Arg  Tyr  Ile  Tyr  Pro  Leu  Asp  Ser
       1610                1615                1620

Leu  Thr  Trp  Ile  Glu  Tyr  Trp  Pro  Arg  Asp  Thr  Thr  Cys  Ser  Ser
       1625                1630                1635

Cys  Gln  Ala  Phe  Leu  Ala  Asn  Leu  Asp  Glu  Phe  Ala  Glu  Asp  Ile
       1640                1645                1650

Phe  Leu  Asn  Gly  Cys
       1655

<210> SEQ ID NO 3
<211> LENGTH: 999
<212> TYPE: PRT
<213> ORGANISM: Homo sapiens

<400> SEQUENCE: 3

Thr  Leu  Gln  Lys  Lys  Ile  Glu  Glu  Ile  Ala  Ala  Lys  Tyr  Lys  His  Ser
1                5                  10                  15
```

-continued

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
    35                  40                  45

Lys Ala Phe Thr Glu Cys Cys Val Val Ala Ser Gln Leu Arg Ala Asn
50                  55                  60

Ile Ser His Lys Asp Met Gln Leu Gly Arg Leu His Met Lys Thr Leu
65              70                  75                  80

Leu Pro Val Ser Lys Pro Glu Ile Arg Ser Tyr Phe Pro Glu Ser Trp
                85                  90                  95

Leu Trp Glu Val His Leu Val Pro Arg Arg Lys Gln Leu Gln Phe Ala
            100                 105                 110

Leu Pro Asp Ser Leu Thr Thr Trp Glu Ile Gln Gly Ile Gly Ile Ser
            115                 120                 125

Asn Thr Gly Ile Cys Val Ala Asp Thr Val Lys Ala Lys Val Phe Lys
        130                 135                 140

Asp Val Phe Leu Glu Met Asn Ile Pro Tyr Ser Val Arg Gly Glu
145                 150                 155                 160

Gln Ile Gln Leu Lys Gly Thr Val Tyr Asn Tyr Arg Thr Ser Gly Met
                165                 170                 175

Gln Phe Cys Val Lys Met Ser Ala Val Glu Gly Ile Cys Thr Ser Glu
            180                 185                 190

Ser Pro Val Ile Asp His Gln Gly Thr Lys Ser Ser Lys Cys Val Arg
        195                 200                 205

Gln Lys Val Glu Gly Ser Ser His Leu Val Thr Phe Thr Val Leu
210                 215                 220

Pro Leu Glu Ile Gly Leu His Asn Ile Asn Phe Ser Leu Glu Thr Trp
225                 230                 235                 240

Phe Gly Lys Glu Ile Leu Val Lys Thr Leu Arg Val Val Pro Glu Gly
                245                 250                 255

Val Lys Arg Glu Ser Tyr Ser Gly Val Thr Leu Asp Pro Arg Gly Ile
            260                 265                 270

Tyr Gly Thr Ile Ser Arg Arg Lys Glu Phe Pro Tyr Arg Ile Pro Leu
        275                 280                 285

Asp Leu Val Pro Lys Thr Glu Ile Lys Arg Ile Leu Ser Val Lys Gly
290                 295                 300

Leu Leu Val Gly Glu Ile Leu Ser Ala Val Leu Ser Gln Glu Gly Ile
305                 310                 315                 320

Asn Ile Leu Thr His Leu Pro Lys Gly Ser Ala Glu Ala Glu Leu Met
                325                 330                 335

Ser Val Val Pro Val Phe Tyr Val Phe His Tyr Leu Glu Thr Gly Asn
            340                 345                 350

His Trp Asn Ile Phe His Ser Asp Pro Leu Ile Glu Lys Gln Lys Leu
        355                 360                 365

Lys Lys Lys Leu Lys Glu Gly Met Leu Ser Ile Met Ser Tyr Arg Asn
370                 375                 380

Ala Asp Tyr Ser Tyr Ser Val Trp Lys Gly Gly Ser Ala Ser Thr Trp
385                 390                 395                 400

Leu Thr Ala Phe Ala Leu Arg Val Leu Gly Gln Val Asn Lys Tyr Val
                405                 410                 415

Glu Gln Asn Gln Asn Ser Ile Cys Asn Ser Leu Leu Trp Leu Val Glu
            420                 425                 430

Asn Tyr Gln Leu Asp Asn Gly Ser Phe Lys Glu Asn Ser Gln Tyr Gln

```
                435                 440                 445
Pro Ile Lys Leu Gln Gly Thr Leu Pro Val Glu Ala Arg Glu Asn Ser
450                 455                 460

Leu Tyr Leu Thr Ala Phe Thr Val Ile Gly Ile Arg Lys Ala Phe Asp
465                 470                 475                 480

Ile Cys Pro Leu Val Lys Ile Asp Thr Ala Leu Ile Lys Ala Asp Asn
                485                 490                 495

Phe Leu Leu Glu Asn Thr Leu Pro Ala Gln Ser Thr Phe Thr Leu Ala
                500                 505                 510

Ile Ser Ala Tyr Ala Leu Ser Leu Gly Asp Lys Thr His Pro Gln Phe
                515                 520                 525

Arg Ser Ile Val Ser Ala Leu Lys Arg Glu Ala Leu Val Lys Gly Asn
530                 535                 540

Pro Pro Ile Tyr Arg Phe Trp Lys Asp Asn Leu Gln His Lys Asp Ser
545                 550                 555                 560

Ser Val Pro Asn Thr Gly Thr Ala Arg Met Val Glu Thr Thr Ala Tyr
                565                 570                 575

Ala Leu Leu Thr Ser Leu Asn Leu Lys Asp Ile Asn Tyr Val Asn Pro
                580                 585                 590

Val Ile Lys Trp Leu Ser Glu Glu Gln Arg Tyr Gly Gly Phe Tyr
                595                 600                 605

Ser Thr Gln Asp Thr Ile Asn Ala Ile Glu Gly Leu Thr Glu Tyr Ser
                610                 615                 620

Leu Leu Val Lys Gln Leu Arg Leu Ser Met Asp Ile Asp Val Ser Tyr
625                 630                 635                 640

Lys His Lys Gly Ala Leu His Asn Tyr Lys Met Thr Asp Lys Asn Phe
                645                 650                 655

Leu Gly Arg Pro Val Glu Val Leu Leu Asn Asp Asp Leu Ile Val Ser
                660                 665                 670

Thr Gly Phe Gly Ser Gly Leu Ala Thr Val His Val Thr Thr Val Val
                675                 680                 685

His Lys Thr Ser Thr Ser Glu Glu Val Cys Ser Phe Tyr Leu Lys Ile
                690                 695                 700

Asp Thr Gln Asp Ile Glu Ala Ser His Tyr Arg Gly Tyr Gly Asn Ser
705                 710                 715                 720

Asp Tyr Lys Arg Ile Val Ala Cys Ala Ser Tyr Lys Pro Ser Arg Glu
                725                 730                 735

Glu Ser Ser Ser Gly Ser Ser His Ala Val Met Asp Ile Ser Leu Pro
                740                 745                 750

Thr Gly Ile Ser Ala Asn Glu Glu Asp Leu Lys Ala Leu Val Glu Gly
                755                 760                 765

Val Asp Gln Leu Phe Thr Asp Tyr Gln Ile Lys Asp Gly His Val Ile
770                 775                 780

Leu Gln Leu Asn Ser Ile Pro Ser Ser Asp Phe Leu Cys Val Arg Phe
785                 790                 795                 800

Arg Ile Phe Glu Leu Phe Glu Val Gly Phe Leu Ser Pro Ala Thr Phe
                805                 810                 815

Thr Val Tyr Glu Tyr His Arg Pro Asp Lys Gln Cys Thr Met Phe Tyr
                820                 825                 830

Ser Thr Ser Asn Ile Lys Ile Gln Lys Val Cys Glu Gly Ala Ala Cys
                835                 840                 845

Lys Cys Val Glu Ala Asp Cys Gly Gln Met Gln Glu Glu Leu Asp Leu
850                 855                 860
```

```
Thr Ile Ser Ala Glu Thr Arg Lys Gln Thr Ala Cys Lys Pro Glu Ile
865                 870                 875                 880

Ala Tyr Ala Tyr Lys Val Ser Ile Thr Ser Ile Thr Val Glu Asn Val
            885                 890                 895

Phe Val Lys Tyr Lys Ala Thr Leu Leu Asp Ile Tyr Lys Thr Gly Glu
            900                 905                 910

Ala Val Ala Glu Lys Asp Ser Glu Ile Thr Phe Ile Lys Lys Val Thr
            915                 920                 925

Cys Thr Asn Ala Glu Leu Val Lys Gly Arg Gln Tyr Leu Ile Met Gly
        930                 935                 940

Lys Glu Ala Leu Gln Ile Lys Tyr Asn Phe Ser Phe Arg Tyr Ile Tyr
945                 950                 955                 960

Pro Leu Asp Ser Leu Thr Trp Ile Glu Tyr Trp Pro Arg Asp Thr Thr
                965                 970                 975

Cys Ser Ser Cys Gln Ala Phe Leu Ala Asn Leu Asp Glu Phe Ala Glu
            980                 985                 990

Asp Ile Phe Leu Asn Gly Cys
            995
```

<210> SEQ ID NO 4
<211> LENGTH: 655
<212> TYPE: PRT
<213> ORGANISM: Homo sapiens

<400> SEQUENCE: 4

```
Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
            20                  25                  30

Asp Ala Thr Ile Ser Ile Lys Ser Tyr Pro Asp Lys Lys Phe Ser Tyr
        35                  40                  45

Ser Ser Gly His Val His Leu Ser Ser Glu Asn Lys Phe Gln Asn Ser
    50                  55                  60

Ala Ile Leu Thr Ile Gln Pro Lys Gln Leu Pro Gly Gly Gln Asn Pro
65                  70                  75                  80

Val Ser Tyr Val Tyr Leu Glu Val Val Ser Lys His Phe Ser Lys Ser
                85                  90                  95

Lys Arg Met Pro Ile Thr Tyr Asp Asn Gly Phe Leu Phe Ile His Thr
            100                 105                 110

Asp Lys Pro Val Tyr Thr Pro Asp Gln Ser Val Lys Val Arg Val Tyr
        115                 120                 125

Ser Leu Asn Asp Asp Leu Lys Pro Ala Lys Arg Glu Thr Val Leu Thr
    130                 135                 140

Phe Ile Asp Pro Glu Gly Ser Glu Val Asp Met Val Glu Glu Ile Asp
145                 150                 155                 160

His Ile Gly Ile Ile Ser Phe Pro Asp Phe Lys Ile Pro Ser Asn Pro
                165                 170                 175

Arg Tyr Gly Met Trp Thr Ile Lys Ala Lys Tyr Lys Glu Asp Phe Ser
            180                 185                 190

Thr Thr Gly Thr Ala Tyr Phe Glu Val Lys Glu Tyr Val Leu Pro His
        195                 200                 205

Phe Ser Val Ser Ile Glu Pro Glu Tyr Asn Phe Ile Gly Tyr Lys Asn
    210                 215                 220

Phe Lys Asn Phe Glu Ile Thr Ile Lys Ala Arg Tyr Phe Tyr Asn Lys
```

```
            225                 230                 235                 240
Val Val Thr Glu Ala Asp Val Tyr Ile Thr Phe Gly Ile Arg Glu Asp
                    245                 250                 255
Leu Lys Asp Asp Gln Lys Glu Met Met Gln Thr Ala Met Gln Asn Thr
                    260                 265                 270
Met Leu Ile Asn Gly Ile Ala Gln Val Thr Phe Asp Ser Glu Thr Ala
                    275                 280                 285
Val Lys Glu Leu Ser Tyr Tyr Ser Leu Glu Asp Leu Asn Asn Lys Tyr
                    290                 295                 300
Leu Tyr Ile Ala Val Thr Val Ile Glu Ser Thr Gly Gly Phe Ser Glu
305                 310                 315                 320
Glu Ala Glu Ile Pro Gly Ile Lys Tyr Val Leu Ser Pro Tyr Lys Leu
                    325                 330                 335
Asn Leu Val Ala Thr Pro Leu Phe Leu Lys Pro Gly Ile Pro Tyr Pro
                    340                 345                 350
Ile Lys Val Gln Val Lys Asp Ser Leu Asp Gln Leu Val Gly Gly Val
                    355                 360                 365
Pro Val Ile Leu Asn Ala Gln Thr Ile Asp Val Asn Gln Glu Thr Ser
370                 375                 380
Asp Leu Asp Pro Ser Lys Ser Val Thr Arg Val Asp Asp Gly Val Ala
385                 390                 395                 400
Ser Phe Val Leu Asn Leu Pro Ser Gly Val Thr Val Leu Glu Phe Asn
                    405                 410                 415
Val Lys Thr Asp Ala Pro Asp Leu Pro Glu Glu Asn Gln Ala Arg Glu
                    420                 425                 430
Gly Tyr Arg Ala Ile Ala Tyr Ser Ser Leu Ser Gln Ser Tyr Leu Tyr
                    435                 440                 445
Ile Asp Trp Thr Asp Asn His Lys Ala Leu Leu Val Gly Glu His Leu
                    450                 455                 460
Asn Ile Ile Val Thr Pro Lys Ser Pro Tyr Ile Asp Lys Ile Thr His
465                 470                 475                 480
Tyr Asn Tyr Leu Ile Leu Ser Lys Gly Lys Ile Ile His Phe Gly Thr
                    485                 490                 495
Arg Glu Lys Phe Ser Asp Ala Ser Tyr Gln Ser Ile Asn Ile Pro Val
                    500                 505                 510
Thr Gln Asn Met Val Pro Ser Ser Arg Leu Leu Val Tyr Tyr Ile Val
                    515                 520                 525
Thr Gly Glu Gln Thr Ala Glu Leu Val Ser Asp Ser Val Trp Leu Asn
                    530                 535                 540
Ile Glu Glu Lys Cys Gly Asn Gln Leu Gln Val His Leu Ser Pro Asp
545                 550                 555                 560
Ala Asp Ala Tyr Ser Pro Gly Gln Thr Val Ser Leu Asn Met Ala Thr
                    565                 570                 575
Gly Met Asp Ser Trp Val Ala Leu Ala Ala Val Asp Ser Ala Val Tyr
                    580                 585                 590
Gly Val Gln Arg Gly Ala Lys Lys Pro Leu Glu Arg Val Phe Gln Phe
                    595                 600                 605
Leu Glu Lys Ser Asp Leu Gly Cys Gly Ala Gly Gly Gly Leu Asn Asn
                    610                 615                 620
Ala Asn Val Phe His Leu Ala Gly Leu Thr Phe Leu Thr Asn Ala Asn
625                 630                 635                 640
Ala Asp Asp Ser Gln Glu Asn Asp Glu Pro Cys Lys Glu Ile Leu
                    645                 650                 655
```

<210> SEQ ID NO 5
<211> LENGTH: 21
<212> TYPE: PRT
<213> ORGANISM: Homo sapiens

<400> SEQUENCE: 5

```
Val Ile Asp His Gln Gly Thr Lys Ser Ser Lys Cys Val Arg Gln Lys
1               5                   10                  15

Val Glu Gly Ser Ser
            20
```

<210> SEQ ID NO 6
<211> LENGTH: 5
<212> TYPE: PRT
<213> ORGANISM: Homo sapiens

<400> SEQUENCE: 6

```
Lys Ser Ser Lys Cys
1               5
```

<210> SEQ ID NO 7
<211> LENGTH: 127
<212> TYPE: PRT
<213> ORGANISM: Homo sapiens

<400> SEQUENCE: 7

```
Asn Phe Ser Leu Glu Thr Trp Phe Gly Lys Glu Ile Leu Val Lys Thr
1               5                   10                  15

Leu Arg Val Val Pro Glu Gly Val Lys Arg Glu Ser Tyr Ser Gly Val
            20                  25                  30

Thr Leu Asp Pro Arg Gly Ile Tyr Gly Thr Ile Ser Arg Arg Lys Glu
        35                  40                  45

Phe Pro Tyr Arg Ile Pro Leu Asp Leu Val Pro Lys Thr Glu Ile Lys
    50                  55                  60

Arg Ile Leu Ser Val Lys Gly Leu Leu Val Gly Glu Ile Leu Ser Ala
65                  70                  75                  80

Val Leu Ser Gln Glu Gly Ile Asn Ile Leu Thr His Leu Pro Lys Gly
                85                  90                  95

Ser Ala Glu Ala Glu Leu Met Ser Val Val Pro Val Phe Tyr Val Phe
            100                 105                 110

His Tyr Leu Glu Thr Gly Asn His Trp Asn Ile Phe His Ser Asp
        115                 120                 125
```

<210> SEQ ID NO 8
<211> LENGTH: 200
<212> TYPE: PRT
<213> ORGANISM: Homo sapiens

<400> SEQUENCE: 8

```
Ser Glu Ser Pro Val Ile Asp His Gln Gly Thr Lys Ser Ser Lys Cys
1               5                   10                  15

Val Arg Gln Lys Val Glu Gly Ser Ser Ser His Leu Val Thr Phe Thr
            20                  25                  30

Val Leu Pro Leu Glu Ile Gly Leu His Asn Ile Asn Phe Ser Leu Glu
        35                  40                  45

Thr Trp Phe Gly Lys Glu Ile Leu Val Lys Thr Leu Arg Val Val Pro
    50                  55                  60

Glu Gly Val Lys Arg Glu Ser Tyr Ser Gly Val Thr Leu Asp Pro Arg
```

```
                65                  70                  75                  80
Gly Ile Tyr Gly Thr Ile Ser Arg Arg Lys Glu Phe Pro Tyr Arg Ile
                85                  90                  95

Pro Leu Asp Leu Val Pro Lys Thr Glu Ile Lys Arg Ile Leu Ser Val
            100                 105                 110

Lys Gly Leu Leu Val Gly Glu Ile Leu Ser Ala Val Leu Ser Gln Glu
        115                 120                 125

Gly Ile Asn Ile Leu Thr His Leu Pro Lys Gly Ser Ala Glu Ala Glu
    130                 135                 140

Leu Met Ser Val Val Pro Val Phe Tyr Val Phe His Tyr Leu Glu Thr
145                 150                 155                 160

Gly Asn His Trp Asn Ile Phe His Ser Asp Pro Leu Ile Glu Lys Gln
                165                 170                 175

Lys Leu Lys Lys Lys Leu Lys Glu Gly Met Leu Ser Ile Met Ser Tyr
            180                 185                 190

Arg Asn Ala Asp Tyr Ser Tyr Ser
        195                 200

<210> SEQ ID NO 9
<211> LENGTH: 30
<212> TYPE: PRT
<213> ORGANISM: Homo sapiens

<400> SEQUENCE: 9

Ser His Lys Asp Met Gln Leu Gly Arg Leu His Met Lys Thr Leu Leu
1               5                   10                  15

Pro Val Ser Lys Pro Glu Ile Arg Ser Tyr Phe Pro Glu Ser
            20                  25                  30

<210> SEQ ID NO 10
<211> LENGTH: 325
<212> TYPE: PRT
<213> ORGANISM: Homo sapiens

<400> SEQUENCE: 10

Ser His Lys Asp Met Gln Leu Gly Arg Leu His Met Lys Thr Leu Leu
1               5                   10                  15

Pro Val Ser Lys Pro Glu Ile Arg Ser Tyr Phe Pro Glu Ser Trp Leu
            20                  25                  30

Trp Glu Val His Leu Val Pro Arg Arg Lys Gln Leu Gln Phe Ala Leu
        35                  40                  45

Pro Asp Ser Leu Thr Thr Trp Glu Ile Gln Gly Ile Gly Ile Ser Asn
    50                  55                  60

Thr Gly Ile Cys Val Ala Asp Thr Val Lys Ala Lys Val Phe Lys Asp
65                  70                  75                  80

Val Phe Leu Glu Met Asn Ile Pro Tyr Ser Val Val Arg Gly Glu Gln
                85                  90                  95

Ile Gln Leu Lys Gly Thr Val Tyr Asn Tyr Arg Thr Ser Gly Met Gln
            100                 105                 110

Phe Cys Val Lys Met Ser Ala Val Glu Gly Ile Cys Thr Ser Glu Ser
        115                 120                 125

Pro Val Ile Asp His Gln Gly Thr Lys Ser Ser Lys Cys Val Arg Gln
    130                 135                 140

Lys Val Glu Gly Ser Ser Ser His Leu Val Thr Phe Thr Val Leu Pro
145                 150                 155                 160

Leu Glu Ile Gly Leu His Asn Ile Asn Phe Ser Leu Glu Thr Trp Phe
```

```
                165                 170                 175
Gly Lys Glu Ile Leu Val Lys Thr Leu Arg Val Pro Glu Gly Val
                180                 185                 190

Lys Arg Glu Ser Tyr Ser Gly Val Thr Leu Asp Pro Arg Gly Ile Tyr
                195                 200                 205

Gly Thr Ile Ser Arg Arg Lys Glu Phe Pro Tyr Arg Ile Pro Leu Asp
            210                 215                 220

Leu Val Pro Lys Thr Glu Ile Lys Arg Ile Leu Ser Val Lys Gly Leu
225                 230                 235                 240

Leu Val Gly Glu Ile Leu Ser Ala Val Leu Ser Gln Glu Gly Ile Asn
                245                 250                 255

Ile Leu Thr His Leu Pro Lys Gly Ser Ala Glu Ala Glu Leu Met Ser
                260                 265                 270

Val Val Pro Val Phe Tyr Val Phe His Tyr Leu Glu Thr Gly Asn His
                275                 280                 285

Trp Asn Ile Phe His Ser Asp Pro Leu Ile Glu Lys Gln Lys Leu Lys
                290                 295                 300

Lys Lys Leu Lys Glu Gly Met Leu Ser Ile Met Ser Tyr Arg Asn Ala
305                 310                 315                 320

Asp Tyr Ser Tyr Ser
                325
```

<210> SEQ ID NO 11
<211> LENGTH: 17
<212> TYPE: PRT
<213> ORGANISM: Homo sapiens

<400> SEQUENCE: 11

```
Asp His Gln Gly Thr Lys Ser Ser Lys Cys Val Arg Gln Lys Val Glu
1               5                   10                  15

Gly
```

<210> SEQ ID NO 12
<211> LENGTH: 74
<212> TYPE: PRT
<213> ORGANISM: Homo sapiens

<400> SEQUENCE: 12

```
Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
        50                  55                  60

Ile Ser His Lys Asp Met Gln Leu Gly Arg
65                  70
```

<210> SEQ ID NO 13
<211> LENGTH: 20
<212> TYPE: PRT
<213> ORGANISM: Homo sapiens

<400> SEQUENCE: 13

```
Cys Cys Tyr Asp Gly Ala Cys Val Asn Asn Asp Glu Thr Cys Glu Gln
1               5                   10                  15
```

Arg Ala Ala Arg
         20

<210> SEQ ID NO 14
<211> LENGTH: 18
<212> TYPE: PRT
<213> ORGANISM: Homo sapiens

<400> SEQUENCE: 14

Lys Cys Cys Tyr Asp Gly Ala Cys Val Asn Asn Asp Glu Thr Cys Glu
1               5                   10                  15

Gln Arg

<210> SEQ ID NO 15
<211> LENGTH: 10
<212> TYPE: PRT
<213> ORGANISM: Homo sapiens

<400> SEQUENCE: 15

Val Asn Asn Asp Glu Thr Cys Glu Gln Arg
1               5                   10

<210> SEQ ID NO 16
<211> LENGTH: 6
<212> TYPE: PRT
<213> ORGANISM: Homo sapiens

<400> SEQUENCE: 16

Val Asn Asn Asp Glu Thr
1               5

<210> SEQ ID NO 17
<211> LENGTH: 9
<212> TYPE: PRT
<213> ORGANISM: Homo sapiens

<400> SEQUENCE: 17

Ala Ala Arg Ile Ser Leu Gly Pro Arg
1               5

<210> SEQ ID NO 18
<211> LENGTH: 19
<212> TYPE: PRT
<213> ORGANISM: Homo sapiens

<400> SEQUENCE: 18

Cys Cys Tyr Asp Gly Ala Cys Val Asn Asn Asp Glu Thr Cys Glu Gln
1               5                   10                  15

Arg Ala Ala

<210> SEQ ID NO 19
<211> LENGTH: 18
<212> TYPE: PRT
<213> ORGANISM: Homo sapiens

<400> SEQUENCE: 19

Cys Cys Tyr Asp Gly Ala Cys Val Asn Asn Asp Glu Thr Cys Glu Gln
1               5                   10                  15

Arg Ala

<210> SEQ ID NO 20
<211> LENGTH: 17
<212> TYPE: PRT

-continued

<213> ORGANISM: Homo sapiens

<400> SEQUENCE: 20

Cys Cys Tyr Asp Gly Ala Cys Val Asn Asn Asp Glu Thr Cys Glu Gln
1               5                   10                  15

Arg

<210> SEQ ID NO 21
<211> LENGTH: 16
<212> TYPE: PRT
<213> ORGANISM: Homo sapiens

<400> SEQUENCE: 21

Cys Cys Tyr Asp Gly Ala Cys Val Asn Asn Asp Glu Thr Cys Glu Gln
1               5                   10                  15

<210> SEQ ID NO 22
<211> LENGTH: 15
<212> TYPE: PRT
<213> ORGANISM: Homo sapiens

<400> SEQUENCE: 22

Cys Cys Tyr Asp Gly Ala Cys Val Asn Asn Asp Glu Thr Cys Glu
1               5                   10                  15

<210> SEQ ID NO 23
<211> LENGTH: 19
<212> TYPE: PRT
<213> ORGANISM: Homo sapiens

<400> SEQUENCE: 23

Cys Tyr Asp Gly Ala Cys Val Asn Asn Asp Glu Thr Cys Glu Gln Arg
1               5                   10                  15

Ala Ala Arg

<210> SEQ ID NO 24
<211> LENGTH: 18
<212> TYPE: PRT
<213> ORGANISM: Homo sapiens

<400> SEQUENCE: 24

Tyr Asp Gly Ala Cys Val Asn Asn Asp Glu Thr Cys Glu Gln Arg Ala
1               5                   10                  15

Ala Arg

<210> SEQ ID NO 25
<211> LENGTH: 19
<212> TYPE: PRT
<213> ORGANISM: Homo sapiens

<400> SEQUENCE: 25

Cys Tyr Asp Gly Ala Cys Val Asn Asn Asp Glu Thr Cys Glu Gln Arg
1               5                   10                  15

Ala Ala Arg

<210> SEQ ID NO 26
<211> LENGTH: 925
<212> TYPE: PRT
<213> ORGANISM: Homo sapiens

<400> SEQUENCE: 26

Leu His Met Lys Thr Leu Leu Pro Val Ser Lys Pro Glu Ile Arg Ser

```
1               5                   10                  15
Tyr Phe Pro Glu Ser Trp Leu Trp Glu Val His Leu Val Pro Arg Arg
            20                  25                  30
Lys Gln Leu Gln Phe Ala Leu Pro Asp Ser Leu Thr Thr Trp Glu Ile
            35                  40                  45
Gln Gly Ile Gly Ile Ser Asn Thr Gly Ile Cys Val Ala Asp Thr Val
            50                  55                  60
Lys Ala Lys Val Phe Lys Asp Val Phe Leu Glu Met Asn Ile Pro Tyr
65                  70                  75                  80
Ser Val Val Arg Gly Glu Gln Ile Gln Leu Lys Gly Thr Val Tyr Asn
                85                  90                  95
Tyr Arg Thr Ser Gly Met Gln Phe Cys Val Lys Met Ser Ala Val Glu
                100                 105                 110
Gly Ile Cys Thr Ser Glu Ser Pro Val Ile Asp His Gln Gly Thr Lys
                115                 120                 125
Ser Ser Lys Cys Val Arg Gln Lys Val Glu Gly Ser Ser Ser His Leu
        130                 135                 140
Val Thr Phe Thr Val Leu Pro Leu Glu Ile Gly Leu His Asn Ile Asn
145                 150                 155                 160
Phe Ser Leu Glu Thr Trp Phe Gly Lys Glu Ile Leu Val Lys Thr Leu
                165                 170                 175
Arg Val Val Pro Glu Gly Val Lys Arg Glu Ser Tyr Ser Gly Val Thr
                180                 185                 190
Leu Asp Pro Arg Gly Ile Tyr Gly Thr Ile Ser Arg Arg Lys Glu Phe
            195                 200                 205
Pro Tyr Arg Ile Pro Leu Asp Leu Val Pro Lys Thr Glu Ile Lys Arg
        210                 215                 220
Ile Leu Ser Val Lys Gly Leu Leu Val Gly Ile Leu Ser Ala Val
225                 230                 235                 240
Leu Ser Gln Glu Gly Ile Asn Ile Leu Thr His Leu Pro Lys Gly Ser
                245                 250                 255
Ala Glu Ala Glu Leu Met Ser Val Val Pro Val Phe Tyr Val Phe His
                260                 265                 270
Tyr Leu Glu Thr Gly Asn His Trp Asn Ile Phe His Ser Asp Pro Leu
            275                 280                 285
Ile Glu Lys Gln Lys Leu Lys Lys Lys Leu Lys Glu Gly Met Leu Ser
        290                 295                 300
Ile Met Ser Tyr Arg Asn Ala Asp Tyr Ser Tyr Ser Val Trp Lys Gly
305                 310                 315                 320
Gly Ser Ala Ser Thr Trp Leu Thr Ala Phe Ala Leu Arg Val Leu Gly
                325                 330                 335
Gln Val Asn Lys Tyr Val Glu Gln Asn Gln Ser Ile Cys Asn Ser
                340                 345                 350
Leu Leu Trp Leu Val Glu Asn Tyr Gln Leu Asp Asn Gly Ser Phe Lys
            355                 360                 365
Glu Asn Ser Gln Tyr Gln Pro Ile Lys Leu Gln Gly Thr Leu Pro Val
        370                 375                 380
Glu Ala Arg Glu Asn Ser Leu Tyr Leu Thr Ala Phe Thr Val Ile Gly
385                 390                 395                 400
Ile Arg Lys Ala Phe Asp Ile Cys Pro Leu Val Lys Ile Asp Thr Ala
                405                 410                 415
Leu Ile Lys Ala Asp Asn Phe Leu Leu Glu Asn Thr Leu Pro Ala Gln
            420                 425                 430
```

-continued

```
Ser Thr Phe Thr Leu Ala Ile Ser Ala Tyr Ala Leu Ser Leu Gly Asp
            435                 440                 445

Lys Thr His Pro Gln Phe Arg Ser Ile Val Ser Ala Leu Lys Arg Glu
450                 455                 460

Ala Leu Val Lys Gly Asn Pro Pro Ile Tyr Arg Phe Trp Lys Asp Asn
465                 470                 475                 480

Leu Gln His Lys Asp Ser Ser Val Pro Asn Thr Gly Thr Ala Arg Met
            485                 490                 495

Val Glu Thr Thr Ala Tyr Ala Leu Leu Thr Ser Leu Asn Leu Lys Asp
            500                 505                 510

Ile Asn Tyr Val Asn Pro Val Ile Lys Trp Leu Ser Glu Glu Gln Arg
            515                 520                 525

Tyr Gly Gly Gly Phe Tyr Ser Thr Gln Asp Thr Ile Asn Ala Ile Glu
            530                 535                 540

Gly Leu Thr Glu Tyr Ser Leu Leu Val Lys Gln Leu Arg Leu Ser Met
545                 550                 555                 560

Asp Ile Asp Val Ser Tyr Lys His Lys Gly Ala Leu His Asn Tyr Lys
            565                 570                 575

Met Thr Asp Lys Asn Phe Leu Gly Arg Pro Val Glu Val Leu Leu Asn
            580                 585                 590

Asp Asp Leu Ile Val Ser Thr Gly Phe Gly Ser Gly Leu Ala Thr Val
            595                 600                 605

His Val Thr Thr Val Val His Lys Thr Ser Thr Ser Glu Glu Val Cys
            610                 615                 620

Ser Phe Tyr Leu Lys Ile Asp Thr Gln Asp Ile Glu Ala Ser His Tyr
625                 630                 635                 640

Arg Gly Tyr Gly Asn Ser Asp Tyr Lys Arg Ile Val Ala Cys Ala Ser
            645                 650                 655

Tyr Lys Pro Ser Arg Glu Glu Ser Ser Gly Ser Ser His Ala Val
            660                 665                 670

Met Asp Ile Ser Leu Pro Thr Gly Ile Ser Ala Asn Glu Glu Asp Leu
            675                 680                 685

Lys Ala Leu Val Glu Gly Val Asp Gln Leu Phe Thr Asp Tyr Gln Ile
690                 695                 700

Lys Asp Gly His Val Ile Leu Gln Leu Asn Ser Ile Pro Ser Ser Asp
705                 710                 715                 720

Phe Leu Cys Val Arg Phe Arg Ile Phe Glu Leu Phe Glu Val Gly Phe
            725                 730                 735

Leu Ser Pro Ala Thr Phe Thr Val Tyr Glu Tyr His Arg Pro Asp Lys
            740                 745                 750

Gln Cys Thr Met Phe Tyr Ser Thr Ser Asn Ile Lys Ile Gln Lys Val
            755                 760                 765

Cys Glu Gly Ala Ala Cys Lys Cys Val Glu Ala Asp Cys Gly Gln Met
            770                 775                 780

Gln Glu Glu Leu Asp Leu Thr Ile Ser Ala Glu Thr Arg Lys Gln Thr
785                 790                 795                 800

Ala Cys Lys Pro Glu Ile Ala Tyr Ala Tyr Lys Val Ser Ile Thr Ser
            805                 810                 815

Ile Thr Val Glu Asn Val Phe Val Lys Tyr Lys Ala Thr Leu Leu Asp
            820                 825                 830

Ile Tyr Lys Thr Gly Glu Ala Val Ala Glu Lys Asp Ser Glu Ile Thr
            835                 840                 845
```

-continued

```
Phe Ile Lys Lys Val Thr Cys Thr Asn Ala Glu Leu Val Lys Gly Arg
    850             855             860
Gln Tyr Leu Ile Met Gly Lys Glu Ala Leu Gln Ile Lys Tyr Asn Phe
865             870             875             880
Ser Phe Arg Tyr Ile Tyr Pro Leu Asp Ser Leu Thr Trp Ile Glu Tyr
            885             890             895
Trp Pro Arg Asp Thr Thr Cys Ser Ser Cys Gln Ala Phe Leu Ala Asn
            900             905             910
Leu Asp Glu Phe Ala Glu Asp Ile Phe Leu Asn Gly Cys
        915             920             925
```

US 8,999,340 B2

METHODS FOR TREATING MULTIORGAN, SYSTEMIC DEGOS' DISEASE WITH A COMPLEMENT INHIBITOR

CROSS-REFERENCE TO RELATED APPLICATIONS

This application is a national stage filing under 35 U.S.C. §371 of International Application No. PCT/US2011/026602, filed on Mar. 1, 2011, which claims the benefit of the filing date under 35 U.S.C. §119(e) to U.S. provisional patent application serial no. 61/309,393, filed on Mar. 1,2010, the entire contents of which is hereby incorporated by reference. International Application No. PCT/US2011/026602 was published under PCT Article 21(2) in English.

Sequence Listing

The instant application contains a Sequence Listing which has been submitted via EFS-Web and is hereby incorporated by reference in its entirety. Said ASCII copy, created on Nov. 16, 2012, is named ALXN153301_Seq.txt, and is 61,434 bytes in size.

TECHNICAL FIELD

The field of the invention is medicine, immunology, molecular biology, and protein chemistry.

BACKGROUND

Degos' disease (also known as Kohlmeier disease and malignant atrophic papulosis (MAP)) is a rare vasculopathy (around 200 reported cases) characterized by thrombosis in small to large vessels. See, e.g., Lester and Rapini (2009) *Curr Opin Gastroenterol* 25:66-73 and Englert et al. (1984) *Br Med J* 289:576. Although generally considered to be of unknown etiology, Degos' disease has been associated with viral infections (e.g., B19 parvovirus and HIV) and autoimmune disorders such as lupus erythematosis (LE), dermatomyositis, and primary antiphospholipid syndrome (APS). See, e.g., Crowson et al. (2002) *J Cutan Pathol* 29:596-601; Englert et al. (1984), supra; Heymann (2009) *J Am Acad Dermatol* 61:505-506; Durie et al. (1969) *Arch Dermatol* 100(5):575-581; Tsao et al. (1997) *J Am Acad Dermatol* 36:317-319; and Requena et al. (1998) *J Am Acad Dermatol* 38:852-856. Some forms of Degos' disease may be familial. See, e.g., Katz et al. (1997) *J Am Acad Dermatol* 37:480-484 and Penault et al. (2004) *Ann Dermatol Venereol* 131:989-993. Degos can occur in patients of any age, yet it appears to preferentially affect men over women at a ratio of approximately 3 to 1. See, e.g., Katz et al. (1997), supra; Torrelo et al. (2002) *Br J Dermatol* 146:916-918; and Wilson et al. (2007) *Pediatr Dermatol* 24(1):18-24.

Degos can manifest as a benign, purely cutaneous form or as an aggressive, multiorgan, systemic form, the latter of which is generally fatal within one to twelve years after diagnosis. Scheinfeld (2007) *Clin Exp Derm* 32:483-487. The phenotypic hallmark of cutaneous Degos' disease is the appearance of one or more erythematous, reddish-colored papules on the skin, which papules scar over with white, atrophic centers.

Death occurs in nearly all patients with the systemic form of Degos' disease, the patients having an average life expectancy after systemic involvement of around two to three years. See, e.g., Scheinfeld (2007), supra. Patients usually die from intestinal perforation with or without septic complications; however, death may alternatively result from intestinal infarction, cardiopulmonary collapse, and/or neurological infarction and hemorrhage. Id. See also High et al. (2004) *J Am Acad Dermatol* 50(6):895-899.

A standard medical treatment for Degos' disease has not been defined. Many therapeutic agents have had only marginal and/or inconsistent success in treating the disease. See, e.g., Scheinfeld (2007), supra. For example, some Degos patients benefited from intravenous immunoglobulin therapy, but at present there appears to be no way of predicting which patients would respond to such therapy, see, e.g., Dyrsen et al. (2008) *J Cutan Pathol* 35 (Suppl 1):20-25; Zhu et al. (2007) *Br J Dermatol* 157(1):206-207; and De Breucker et al. (2008) *Acta Clin Belg* 63(2):99-102 (Abstract).

In view of the foregoing, it is clear that there is a need for new approaches and better methods to treat patients with Degos' disease.

SUMMARY

The present disclosure is based, at least in part, on the discovery by the inventor that an inhibitor of complement, namely the humanized anti-C5 antibody eculizumab, was highly efficacious in the treatment of a patient afflicted with the systemic form of Degos' disease. Accordingly, the disclosure features a variety of compositions and methods useful for the prevention and treatment of Degos' disease.

In one aspect, the disclosure provides a method for treating a patient afflicted with Degos' disease, the method comprising administering to a patient afflicted with Degos' disease a complement inhibitor in an amount sufficient to treat the disease.

In another aspect, the disclosure features a method for treating a patient afflicted with Degos' disease, which method includes chronically administering to a patient afflicted with Degos' disease a complement inhibitor in an amount and with a frequency sufficient to maintain a reduced level of complement activity in the patient to thereby treat the disease.

In another aspect, the disclosure features a method for treating Degos' disease, the method comprising: identifying a patient as being, or likely to be, afflicted with Degos' disease; and administering to the patient a complement inhibitor in an amount sufficient to treat the disease.

In another aspect, the disclosure features a method for treating or preventing (e.g., preventing the occurrence of Degos' disease or preventing the progression of the benign cutaneous form of Degos' disease to a more advanced, multiorgan and/or systemic form of the disease). The method includes administering to a patient in need thereof a complement inhibitor in an amount sufficient to treat or prevent the disease. In some embodiments, the inhibitor can be chronically administered in an amount and with a frequency to maintain a reduced level of complement activation in the blood of the patient for the duration of the treatment.

In some embodiments of any of the methods described herein, the Degos' disease is associated with a B19 parvoviral infection or human immunodeficiency virus infection. In some embodiments, the Degos' disease is idiopathic.

In some embodiments of any of the methods described herein, the Degos' disease pathologically affects one or more of the gastrointestinal tract, the central nervous system, and the cardiovascular system. In some embodiments, the Degos' disease is multiorgan, systemic Degos' disease. In some embodiments, the Degos' disease is a cutaneous form of the disease.

In some embodiments of any of the methods described herein, the Degos' disease is refractory to at least one therapy selected from the group consisting of an anti-inflammatory agent, an anticoagulant, an antithrombotic, and intravenous immunoglobulin. The anti-inflammatory drug can be, e.g., one selected from the group consisting of corticosteroids, phenylbutazone, azathioprine, methotrexate, cyclosporine, tacrolimus, and mycophenolate mofetil. The anticoagulant or antithrombotic can be, e.g., one selected from the group consisting of clopidogrel, aspirin, and dipyridamole.

In some embodiments of any of the methods described herein, the complement inhibitor can be, e.g., one selected from the group consisting of a polypeptide, a polypeptide analog, a nucleic acid, a nucleic acid analog, and a small molecule. In some embodiments, the complement inhibitor can be, e.g., one selected from the group consisting of soluble CR1, LEX-CR1, MCP, DAF, CD59, Factor H, cobra venom factor, FUT-175, complestatin, and K76 COOH.

In some embodiments of any of the methods described herein, the complement inhibitor inhibits the expression of a human complement component protein. In some embodiments, the complement inhibitor can inhibit the activity of a complement protein such as, but not limited to, complement component C1s, complement component C1r, the C3 convertase, the C5 convertase, or C5b-9.

In some embodiments of any of the methods described herein, the complement inhibitor inhibits the cleavage of human complement component C5, C4, C3, or C2. For example, a complement inhibitor can inhibit the cleavage of complement component C5 into fragments C5a and C5b.

In some embodiments, the complement inhibitor is an antibody or antigen-binding fragment thereof that binds to a human complement component protein (e.g., a C5 protein). In some embodiments, the antibody or antigen-binding fragment thereof binds to the alpha chain of C5 protein. In some embodiments, the antibody or antigen-binding fragment thereof binds to the beta chain of C5. In some embodiments, the antibody or antigen-binding fragment thereof binds to the alpha chain of human complement component C5, and wherein the antibody (i) inhibits complement activation in a human body fluid, (ii) inhibits the binding of purified human complement component C5 to either human complement component C3b or human complement component C4b, and (iii) does not bind to the human complement activation product free C5a. In some embodiments, the antibody binds to the human complement component C5 protein comprising or consisting of the amino acid sequence depicted in any one of SEQ ID NOs:1-26. In some embodiments, the inhibitor is an antibody or antigen-binding fragment thereof that binds to complement component C5 fragment C5b.

In some embodiments, the antibody can be a monoclonal antibody. In some embodiments, the antibody or antigen-binding fragment thereof can be one selected from the group consisting of a humanized antibody, a recombinant antibody, a diabody, a chimerized or chimeric antibody, a deimmunized human antibody, a fully human antibody, a single chain antibody, an Fv fragment, an Fd fragment, an Fab fragment, an Fab' fragment, and an F(ab')$_2$ fragment.

In some embodiments of any of the methods described herein, the complement inhibitor is eculizumab or pexelizumab.

In yet another aspect, the disclosure features an article of manufacture, which contains: a container comprising a label; and a composition comprising a complement inhibitor, wherein the label indicates that the composition is to be administered to a human having, suspected of having, or at risk for developing, Degos' disease. The inhibitor can be, e.g., an antibody or antigen-binding fragment thereof that binds to a human complement component C5 protein. The inhibitor can be, e.g., an antibody or antigen-binding fragment thereof that binds to a fragment of human complement component C5 protein such as C5a or C5b.

In some embodiments, the article of manufacture includes one or more additional active agents such as, but not limited to, one or more anti-inflammatory agents, anticoagulants, or antithrombotic agents.

The inventor also discovered that the Degos' patient described herein had elevated levels of interferon alpha levels in serum as well as within the biopsied skin tissue. While not being bound by any particular theory or mechanism of action, as interferon alpha upregulates adaptive and innate immunity, potentiating the effects of any antigenic trigger, and administration of exogenous interferon alpha has been reported as a cause of cutaneous thrombosis and ulceration, the inventor believes that inhibiting interferon alpha is a useful strategy for treating Degos' disease.

Accordingly, in another aspect, the disclosure features a method for treating a patient afflicted with Degos' disease, the method comprising administering to a patient afflicted with Degos' disease an inhibitor of interferon alpha in an amount sufficient to treat the disease.

In another aspect, the disclosure features a method for treating a patient afflicted with Degos' disease, the method comprising chronically administering to a patient afflicted with Degos' disease an inhibitor of interferon alpha in an amount and with a frequency sufficient to maintain a reduced level of interferon alpha activity in the patient to thereby treat the disease.

In another aspect, the disclosure features a method for treating Degos' disease, which method includes: identifying a patient as being, or likely to be, afflicted with Degos' disease; and administering to the patient an inhibitor of interferon alpha in an amount sufficient to treat the disease.

In another aspect, the disclosure features a method for treating or preventing (e.g., preventing the occurrence of Degos' disease or preventing the progression of the benign cutaneous form of Degos' disease to a more advanced, multiorgan and/or systemic form of the disease). The method includes administering to a patient in need thereof an inhibitor of interferon alpha in an amount sufficient to treat or prevent the disease. In some embodiments, the inhibitor can be chronically administered in an amount and with a frequency to maintain a reduced level of interferon alpha expression or activity in the blood of the patient for the duration of the treatment.

In some embodiments, the inhibitor of interferon alpha can be, e.g., one selected from the group consisting of a polypeptide, a polypeptide analog, a nucleic acid, a nucleic acid analog, and a small molecule. The inhibitor can, e.g., inhibit the expression of interferon alpha or an interferon alpha receptor by a cell. The inhibitor can, e.g., inhibit the activity of interferon alpha or an interferon alpha receptor protein.

In some embodiments, the inhibitor of interferon alpha binds to interferon alpha. In some embodiments, the inhibitor of interferon alpha binds to an interferon alpha receptor. For example, in some embodiments, the inhibitor of interferon alpha is an antibody (or an antigen-binding fragment thereof) that binds to interferon alpha or to an interferon alpha receptor. The antibody can be a monoclonal antibody. The antibody or antigen-binding fragment thereof can be, e.g., one selected from the group consisting of a humanized antibody, a recombinant antibody, a diabody, a chimerized or chimeric antibody, a deimmunized human antibody, a fully human antibody, a single chain antibody, an Fv fragment, an Fd fragment, an Fab fragment, an Fab' fragment, and an F(ab')$_2$ fragment.

In yet another aspect, the disclosure features an article of manufacture containing: a container comprising a label; and a composition comprising an inhibitor of interferon alpha, wherein the label indicates that the composition is to be administered to a human having, suspected of having, or at risk for developing, Degos' disease. The inhibitor of interferon alpha can be, e.g., any inhibitor of interferon alpha described herein such as an antibody or antigen-binding fragment thereof that binds to interferon alpha or to an interferon receptor.

In some embodiments, the article of manufacture includes one or more additional active agents such as, but not limited to, an anti-inflammatory agent, an anticoagulant, or an anti-thrombotic agent.

In some embodiments, the methods described herein can include administration (either as a single agent or in combination with a complement inhibitor and/or an interferon alpha inhibitor) of a B cell-targeted therapy. For example, the disclosure features a method for treating or preventing Degos' disease, the method comprising administering to a patient having, suspected of having, or at risk for developing, Degos' disease a therapeutically effective amount of a B cell-targeted therapy. The B cell-targeted therapy can be, e.g., an anti-CD20 binding agent such as, but not limited to, anti-CD20 antibodies. Exemplary therapeutic anti-CD20 antibodies, which are approved for clinical use or are in clinical development, that can be used in the methods described herein include, without limitation, rituximab (Biogen Idec®), $^{90}$Y-ibritumomab tiuxetan (Biogen Idec®), $^{131}$I-tositumomab (GlaxoSmithKlin®), ofatumumab (Genmab®), TRU-015 (Trubion®), veltuzumab (IMMU-106; Immunomedics®), ocrelizumab (Roche®), and AME-133v (Applied Molecular Evolution). See, e.g., Levene et al. (2005), supra; Burge et al. (2008) *Clin Ther* 30(10):1806-1816; Kausar et al. (2009) *Expert Opin Biol Ther* 9(7):889-895; Morschhauser et al. (2009) *J Clin Oncol* 27(20):3346-3353; and Milani and Castillo (2009) *Curr Opin Mol Ther* 11(2):200-207.

In another example, any of the methods described herein, e.g., methods in which a complement inhibitor and/or an interferon alpha inhibitor is administered to a Degos' disease patient, the methods can also include administering a B cell-targeted therapy such as an anti-CD20 antibody.

"Polypeptide," "peptide," and "protein" are used interchangeably and mean any peptide-linked chain of amino acids, regardless of length or post-translational modification. The complement component proteins described herein (e.g., complement component C2, C3, C4, or C5 proteins) can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine, and threonine; lysine, histidine and arginine; and phenylalanine and tyrosine.

The human complement component proteins described herein also include "antigenic peptide fragments" of the proteins, which are shorter than full-length, immature (pre-pro) proteins, but retain at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length protein to induce an antigenic response in a mammal. For example, an antigenic peptide fragment of C5 protein can be any fragment of the protein, which is less than the full-length immature protein and retains at least 10% of the ability of the full-length protein to induce an antigenic response in a mammal. Antigenic peptide fragments of a complement component protein include terminal as well internal deletion variants of the protein. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Antigenic peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or 600 or more) amino acid residues in length (e.g., at least 6 contiguous amino acid residues in any one of SEQ ID NOS:1-11). In some embodiments, an antigenic peptide fragment of a human complement component protein is less than 500 (e.g., less than 450, 400, 350, 325, 300, 275, 250, 225, 200, 190, 180, 170, 160, 150, 140, 130, 120, 110, 100, 95, 90, 85, 80, 75, 70, 65, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, or 7) amino acid residues in length (e.g., less than 500 contiguous amino acid residues in any one of SEQ ID NOs:1-11). In some embodiments, an antigenic peptide fragment of a full-length, immature human complement component protein (prepro-C5 protein) is at least 6, but less than 500, amino acid residues in length.

In some embodiments, the human complement component C5 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human C5 protein having the amino acid sequence depicted in SEQ ID NO:1.

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or MegAlign™ (DNASTAR) software. Appropriate parameters for measuring alignment, including any algorithms needed to achieve maximal alignment over the full-length of the sequences being compared can be determined by known methods.

Amino acid sequences for exemplary human C5 proteins as well as antigenic peptide fragments thereof are known in the art and are set forth below.

As used throughout the present disclosure, the term "antibody" refers to a whole or intact antibody (e.g., IgM, IgG, IgA, IgD, or IgE) molecule that is generated by any one of a variety of methods that are known in the art and described herein. The term "antibody" includes a polyclonal antibody, a monoclonal antibody, a chimerized or chimeric antibody, a humanized antibody, a deimmunized human antibody, and a fully human antibody. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to fragment of an antibody that retains the ability to bind to an antigen (e.g., a complement component C5 protein), e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, diabodies (Poljak (1994) *Structure* 2(12):1121-1123; Hudson et al. (1999) *J Immunol Methods* 23(1-2):177-189, the disclosures of both of which are incorporated herein by reference in their entirety) and intrabodies (Huston et al. (2001) *Hum. Antibodies* 10(3-4):127-142; Wheeler et al. (2003) *Mol Ther* 8(3): 355-366; Stocks (2004) *Drug Discov Today* 9(22): 960-966, the disclosures of each of which are incorporated herein by reference in their entirety) that bind to a complement component protein (e.g., complement component C5) can be incorporated into the compositions, and used in the methods, described herein.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating or preventing Degos' disease, will be apparent from the following description, the examples, and from the claims.

DETAILED DESCRIPTION

The present disclosure provides compositions containing an inhibitor of human complement (e.g., an antibody that binds to a human complement component C5 protein) and methods for using the compositions to treat or prevent Degos' disease. While in no way intended to be limiting, exemplary compositions (e.g., pharmaceutical compositions and formulations) and methods for using the compositions are elaborated on below and exemplified in the working Examples.

The Complement Pathway

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16$^{th}$ Edition.

The complement cascade progresses via the classical pathway, the alternative pathway, or the lectin pathway. These pathways share many components, and while they differ in their initial steps, they converge and share the same "terminal complement" components (C5 through C9) responsible for the activation and destruction of target cells.

The classical complement pathway is typically initiated by antibody recognition of, and binding to, an antigenic site on a target cell. The alternative pathway can be antibody independent, and can be initiated by certain molecules on pathogen surfaces. Additionally, the lectin pathway is typically initiated with binding of mannose-binding lectin (MBL) to high mannose substrates. These pathways converge at the point where complement component C3 is cleaved by an active protease (which is different in each pathway) to yield C3a and C3b. Other pathways activating complement attack can act later in the sequence of events leading to various aspects of complement function.

C3a is an anaphylatoxin. C3b binds to bacterial and other cells, as well as to certain viruses and immune complexes, and tags them for removal from the circulation. (C3b in this role is known as opsonin.) The opsonic function of C3b is generally considered to be the most important anti-infective action of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone.

C3b also forms a complex with other components unique to each pathway to form classical or alternative C5 convertase, which cleaves C5 into C5a and C5b. C3 is thus regarded as the central protein in the complement reaction sequence since it is essential to both the alternative and classical pathways. This property of C3b is regulated by the serum protease Factor I, which acts on C3b to produce iC3b. While still functional as opsonin, iC3b cannot form an active C5 convertase.

C5 is a 190 kDa beta globulin found in normal serum at a concentration of approximately 75 µg/mL (0.4 µM). C5 is glycosylated, with about 1.5 to 3 percent of its mass attributed to carbohydrate. Mature C5 is a heterodimer of a 999 amino acid 115 kDa alpha chain that is disulfide linked to a 655 amino acid 75 kDa beta chain. C5 is synthesized as a single chain precursor protein product of a single copy gene (Haviland et al. (1991) *J Immunol* 146:362-368). The cDNA sequence of the transcript of this gene predicts a secreted pro-C5 precursor of 1658 amino acids along with an 18 amino acid leader sequence (see, e.g., U.S. Pat. No. 6,355,245).

The pro-C5 precursor is cleaved after amino acids 655 and 659, to yield the beta chain as an amino terminal fragment (amino acid residues+1 to 655 of the above sequence) and the alpha chain as a carboxyl terminal fragment (amino acid residues 660 to 1658 of the above sequence), with four amino acids (amino acid residues 656-659 of the above sequence) deleted between the two.

C5a is cleaved from the alpha chain of C5 by either alternative or classical C5 convertase as an amino terminal fragment comprising the first 74 amino acids of the alpha chain (i.e., amino acid residues 660-733 of the above sequence). Approximately 20 percent of the 11 kDa mass of C5a is attributed to carbohydrate. The cleavage site for convertase action is at, or immediately adjacent to, amino acid residue 733 of the above sequence. A compound that would bind at, or adjacent, to this cleavage site would have the potential to block access of the C5 convertase enzymes to the cleavage site and thereby act as a complement inhibitor.

C5 can also be activated by means other than C5 convertase activity. Limited trypsin digestion (see, e.g., Minta and Man (1997) *J Immunol* 119:1597-1602 and Wetsel and Kolb (1982) *J Immunol* 128:2209-2216) and acid treatment (Yamamoto and Gewurz (1978) *J Immunol* 120:2008 and Damerau et al. (1989) *Molec Immunol* 26:1133-1142) can also cleave C5 and produce active C5b.

Cleavage of C5 releases C5a, a potent anaphylatoxin and chemotactic factor, and leads to the formation of the lytic terminal complement complex, C5b-9. C5a and C5b-9 also have pleiotropic cell activating properties, by amplifying the release of downstream inflammatory factors, such as hydrolytic enzymes, reactive oxygen species, arachidonic acid metabolites and various cytokines.

C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are anaphylatoxins. These activated complement components can trigger mast cell degranulation, which releases histamine from basophils and mast cells, and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

C5a receptors are found on the surfaces of bronchial and alveolar epithelial cells and bronchial smooth muscle cells. C5a receptors have also been found on eosinophils, mast cells, monocytes, neutrophils, and activated lymphocytes.

Compositions

The compositions described herein can contain an inhibitor of human complement. Any compound which binds to or otherwise blocks the generation and/or activity of any of the human complement components may be utilized in accordance with the present disclosure. For example, an inhibitor of complement can be, e.g., a small molecule, a nucleic acid or nucleic acid analog, a peptidomimetic, or a macromolecule that is not a nucleic acid or a protein. These agents include, but are not limited to, small organic molecules, RNA aptamers, L-RNA aptamers, Spiegelmers, antisense compounds, double stranded RNA, small interfering RNA, locked nucleic acid inhibitors, and peptide nucleic acid inhibitors. In some embodiments, a complement inhibitor may be a protein or protein fragment.

In some embodiments, the compositions contain antibodies specific to a human complement component. Some compounds include antibodies directed against complement components C1, C2, C3, C4, C5 (or a fragment thereof; see below), C6, C7, C8, C9, Factor D, Factor B, Factor P, MBL, MASP-1, or MASP-2, thus preventing the generation of the anaphylatoxic activity associated with C5a and/or preventing the assembly of the membrane attack complex (MAC) associated with C5b. In some embodiments, the inhibitor of complement inhibits the activity and/or assembly of the C5b-9 complex. For example, in some embodiments, the inhibitor is an antibody or an antigen-binding fragment thereof that binds to one of C6, C7, C8, C9, or C5b to thus prevent the assembly and/or activity of the MAC.

The compositions can also contain naturally occurring or soluble forms of complement inhibitory compounds such as CR1, LEX-CR1, MCP, DAF, CD59, Factor H, cobra venom factor, FUT-175, complestatin, and K76 COOH. Other compounds which may be utilized to bind to or otherwise block the generation and/or activity of any of the human complement components include, but are not limited to, proteins, protein fragments, peptides, small molecules, RNA aptamers including ARC 187 (which is commercially available from Archemix Corporation, Cambridge, Mass.), L-RNA aptamers, spiegelmers, antisense compounds, serine protease inhibitors, molecules which may be utilized in RNA interference (RNAi) such as double stranded RNA including small interfering RNA (siRNA), locked nucleic acid (LNA) inhibitors, peptide nucleic acid (PNA) inhibitors, etc.

In some embodiments, the complement inhibitor inhibits the activation of complement. For example, the complement inhibitor can bind to and inhibit the complement activation activity of C1 (e.g., C1q, C1r, or C1s) or the complement inhibitor can bind to and inhibit (e.g., inhibit cleavage of) C2, C3, or C4. In some embodiments, the inhibitor inhibits formation or assembly of the C3 convertase and/or C5 convertase of the alternative and/or classical pathways of complement. In some embodiments, the complement inhibitor inhibits terminal complement formation, e.g., formation of the C5b-9 membrane attack complex. For example, an antibody complement inhibitor may include an anti-C5 antibody. Such anti-C5 antibodies may directly interact with C5 and/or C5b, so as to inhibit the formation of and/or physiologic function of C5b.

In some embodiments, the compositions described herein can contain an inhibitor of human complement component C5 (e.g., an antibody, or antigen-binding fragment thereof, that binds to a human complement component C5 protein or a biologically-active fragment thereof such as C5a or C5b). As used herein, an "inhibitor of complement component C5" is any agent that inhibits: (i) the expression, or proper intracellular trafficking or secretion by a cell, of a complement component C5 protein; (ii) the activity of C5 cleavage fragments C5a or C5b (e.g., the binding of C5a to its cognate cellular receptors or the binding of C5b to C6 and/or other components of the terminal complement complex; see above); (iii) the cleavage of a human C5 protein to form C5a and C5b; or (iv) the proper intracellular trafficking of, or secretion by a cell, of a complement component C5 protein Inhibition of complement component C5 protein expression includes: inhibition of transcription of a gene encoding a human C5 protein; increased degradation of an mRNA encoding a human C5 protein; inhibition of translation of an mRNA encoding a human C5 protein; increased degradation of a human C5 protein; inhibition of proper processing of a pre-pro human C5 protein; or inhibition of proper trafficking or secretion by a cell of a human C5 protein. Methods for determining whether a candidate agent is an inhibitor of human complement component C5 are known in the art and described herein.

An inhibitor of human complement component C5 can be, e.g., a small molecule, a polypeptide, a polypeptide analog, a nucleic acid, or a nucleic acid analog.

"Small molecule" as used herein, is meant to refer to an agent, which has a molecular weight of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J Am Chem Soc* (1998) 120:8565-8566). It is within the scope of this application that such a library may be used to screen for inhibitors of human complement component C5. There are numerous commercially available compound libraries, such as the Chembridge DIVERSet. Libraries are also available from academic investigators, such as the Diversity set from the NCI developmental therapeutics program. Rational drug design may also be employed. For example, rational drug design can employ the use of crystal or solution structural information on the human complement component C5 protein. See, e.g., the structures described in Hagemann et al. (2008) *J Biol Chem* 283(12):7763-75 and Zuiderweg et al. (1989) *Biochemistry* 28(1):172-85. Rational drug design can also be achieved based on known compounds, e.g., a known inhibitor of C5 (e.g., an antibody, or antigen-binding fragment thereof, that binds to a human complement component C5 protein).

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a non-peptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal. It should be noted that peptidomimetics may or may not have similar two-dimensional chemical structures, but share common three-dimensional structural features and geometry. Each peptidomimetic may further have one or more unique additional binding elements.

Nucleic acid inhibitors can be used to decrease expression of an endogenous gene, e.g., a gene encoding human complement component C5. The nucleic acid antagonist can be, e.g., an siRNA, a dsRNA, a ribozyme, a triple-helix former, an aptamer, or an antisense nucleic acid. siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. The siRNA sequences can be, in some embodiments, exactly complementary to the target mRNA. dsRNAs and siRNAs in particular can be used to silence gene expression in mammalian cells (e.g., human cells). See, e.g., Clemens et al. (2000) *Proc Natl Acad Sci USA* 97:6499-6503; Billy et al. (2001) *Proc Natl Acad Sci USA* 98:14428-14433; Elbashir et al. (2001) *Nature* 411:494-8; Yang et al. (2002) *Proc Natl Acad Sci USA* 99:9942-9947, and U.S. Patent Application Publication Nos. 20030166282, 20030143204, 20040038278, and 20030224432. Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted. Hybridization of antisense oligonucleotides with mRNA (e.g., an mRNA encoding a human C5 protein) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA. Exemplary antisense compounds include DNA or RNA sequences that specifically hybridize to the target nucleic acid, e.g., the mRNA encoding a human complement component C5 protein. The complementary region can extend for between about 8 to about 80 nucleobases. The compounds can include one or more modified nucleobases.

Modified nucleobases may include, e.g., 5-substituted pyrimidines such as 5-iodouracil, 5-iodocytosine, and $C_5$—propynyl pyrimidines such as $C_5$-propynylcytosine and $C_5$-propynyluracil. Other suitable modified nucleobases include, e.g., 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. See, e.g., U.S. Pat. Nos. 4,987,071; 5,116,742; and 5,093,246; "Antisense RNA and DNA," D. A. Melton, Ed., Cold Spring Harbor Laboratory, Cold Spring Harbor, N.Y. (1988); Haselhoff and Gerlach (1988) *Nature* 334:585-59; Helene, C. (1991) *Anticancer Drug D* 6:569-84; Helene (1992) *Ann NY Acad Sci* 660:27-36; and Maher (1992) *Bioassays* 14:807-15.

Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers. Aptamers can be made for a wide range of proteins of importance for therapy and diagnostics, such as growth factors and cell surface antigens. These oligonucleotides bind their targets with similar affinities and specificities as antibodies do. See, e.g., Ulrich (2006) *Handb Exp Pharmacol* 173:305-326.

In some embodiments, the inhibitor of human C5 is an antibody, or antigen-binding fragment thereof, which binds to a human complement component C5 protein. (Hereinafter, the antibody may sometimes be referred to as an "anti-C5 antibody.")

In some embodiments, the anti-C5 antibody binds to an epitope in the human pro-C5 precursor protein. For example, the anti-C5 antibody can bind to an epitope in the human complement component C5 protein comprising, or consisting of, the amino acid sequence depicted in SEQ ID NO:1 (NCBI Accession No. AAA51925 and Haviland et al., supra).

An "epitope" refers to the site on a protein (e.g., a human complement component C5 protein) that is bound by an antibody. "Overlapping epitopes" include at least one (e.g., two, three, four, five, or six) common amino acid residue(s).

In some embodiments, the anti-C5 antibody binds to an epitope in the human pro-C5 precursor protein lacking the leader sequence. For example, the anti-C5 antibody can bind to an epitope in the human complement component C5 protein comprising, or consisting of, the amino acid sequence depicted in SEQ ID NO:2, which is a human C5 protein lacking the amino terminal leader sequence.

In some embodiments, the anti-C5 antibody can bind to an epitope in the alpha chain of the human complement component C5 protein. For example, the anti-C5 antibody can bind to an epitope within, or overlapping with, a protein having the amino acid sequence depicted in SEQ ID NO:3, which is the human complement component C5 alpha chain protein. Antibodies that bind to the alpha chain of C5 are described in, for example, Ames et al. (1994) *J Immunol* 152:4572-4581.

In some embodiments, the anti-C5 antibody can bind to an epitope in the beta chain of the human complement component C5 protein. For example, the anti-C5 antibody can bind to an epitope within, or overlapping with, a protein having the amino acid sequence depicted in SEQ ID NO:4, which is the human complement component C5 beta chain protein. Antibodies that bind to the C5 beta chain are described in, e.g., Moongkarndi et al. (1982) *Immunobiol* 162:397; Moongkarndi et al. (1983) *Immunobiol* 165:323; and Mollnes et al. (1988) *Scand J Immunol* 28:307-312.

In some embodiments, the anti-C5 antibody can bind to an epitope within, or overlapping with, an antigenic peptide fragment of a human complement component C5 protein. For example, the anti-C5 antibody can bind to an epitope within, or overlapping with, an antigen peptide fragment of a human complement component C5 protein, the fragment containing, or consisting of, the following amino acid sequence:

```
VIDHQGTKSSKCVRQKVEGSS       (SEQ ID NO: 5)
or

KSSKC.                       (SEQ ID NO: 6)
```

In some embodiments, the anti-C5 antibody can bind to an epitope within, or overlapping with, a fragment of a human complement component C5 protein, the fragment containing, or consisting of, any one of the following amino acid sequences (which are exemplary antigenic fragments of SEQ ID NO:1):

```
                              (SEQ ID NO: 7)
NFSLETWFGKEILVKTLRVVPEGVKRESYSGVTLDPRGIYGTISRRKEFP

YRIPLDLVPKTEIKRILSVKGLLVGEILSAVLSQEGINILTHLPKGSAEA

ELMSVVPVFYVFHYLETGNHWNIFHSD;

(SEQ ID NO: 8)
SESPVIDHQGTKSSKCVRQKVEGSSSHLVTFTVLPLEIGLHNINFSLETW

FGKEILVKTLRVVPEGVKRESYSGVTLDPRGIYGTISRRKEFPYRIPLDL

VPKTEIKRILSVKGLLVGEILSAVLSQEGINILTHLPKGSAEAELMSVVP

VFYVFHYLETGNHWNIFHSDPLIEKQKLKKKLKEGMLSIMSYRNADYSY

S;

(SEQ ID NO: 9)
SHKDMQLGRLHMKTLLPVSKPEIRSYFPES;

(SEQ ID NO: 10)
SHKDMQLGRLHMKTLLPVSKPEIRSYFPESWLWEVHLVPRRKQLQFALPD

SLTTWEIQGIGISNTGICVADTVKAKVFKDVFLEMNIPYSVVRGEQIQLK

GTVYNYRTSGMQFCVKMSAVEGICTSESPVIDHQGTKSSKCVRQKVEGSS

SHLVTFTVLPLEIGLHNINFSLETWFGKEILVKTLRVVPEGVKRESYSGV

TLDPRGIYGTISRRKEFPYRIPLDLVPKTEIKRILSVKGLLVGEILSAVL

SQEGINILTHLPKGSAEAELMSVVPVFYVFHYLETGNHWNIFHSDPLIEK

QKLKKKLKEGMLSIMSYRNADYSYS;
and (SEQ ID NO: 11)
DHQGTKSSKCVRQKVEG.
```

Additional exemplary antigenic fragments of human complement component C5 are disclosed in, e.g., U.S. Pat. No. 6,355,245, the disclosure of which is incorporated herein by reference.

In some embodiments, the anti-C5 antibody specifically binds to a human complement component C5 protein (e.g., the human C5 protein having the amino acid sequence depicted in SEQ ID NO:1). The terms "specific binding" or "specifically binds" refer to two molecules forming a complex (e.g., a complex between an antibody and a complement component C5 protein) that is relatively stable under physiologic conditions. Typically, binding is considered specific when the association constant ($K_a$) is higher than $10^6$ M$^{-1}$. Thus, an antibody can specifically bind to a C5 protein with a $K_a$ of at least (or greater than) $10^6$ (e.g., at least or greater than $10^7$, $10^8$, $10^9$, $10^{10}$, $10^{11}$ $10^{12}$, $10^{13}$, $10^{14}$, or $10^{15}$ or higher) M$^{-1}$. Examples of antibodies that specifically bind to a human complement component C5 protein are described in, e.g., U.S. Pat. No. 6,355,245, the disclosure of which is incorporated herein by reference in its entirety.

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, plasmon surface resonance method (e.g., BIAcore system; Pharmacia Biosensor AB, Uppsala, Sweden and Piscataway, N.J.), or enzyme-linked immunosorbent assays (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2$^{nd}$ Edition, Oxford University Press, NY, Oxford; Johne et al. (1993) *J Immunol Meth* 160:191-198; Jonsson et al. (1993) *Ann Biol Clin* 51:19-26; and Jonsson et al. (1991) *Biotechniques* 11:620-627. See also U.S. Pat. No. 6,355,245.

In some embodiments, the anti-C5 antibody can cross-block binding of another antibody that binds to an epitope within, or overlapping with, a human complement component C5 protein. In some embodiments, the anti-C5 antibody can crossblock binding of an antibody that binds to an epitope within, or overlapping with, a peptide fragment of a human complement component C5 protein. The peptide fragment can be a fragment of a human complement component C5 protein having the amino acid sequence depicted in any one of SEQ ID NOS:1-11. For example, the peptide fragment can contain, or consist of, the following amino acid sequence:

VIDHQGTKSSKCVRQKVEGSS.    (SEQ ID NO: 5)

As used herein, the term "crossblocking antibody" refers to an antibody that lowers the amount of binding of anti-C5 antibody to an epitope on a complement component C5 protein relative to the amount of binding of the anti-C5 antibody to the epitope in the absence of the antibody. Suitable methods for determining whether a first antibody crossblocks binding of a second antibody to an epitope are known in the art. For example, crossblocking antibodies can be identified by comparing the binding of the 5G1.1 anti-C5 monoclonal antibody (produced by the hybridoma cell line ATCC® designation HB-11625; see U.S. Pat. No. 6,355,245) in the presence and absence of a test antibody. Decreased binding of the 5G1.1 antibody in the presence of the test antibody as compared to binding of the 5G1.1 antibody in the absence of the test antibody indicates the test antibody is a crossblocking antibody.

Methods for identifying the epitope to which a particular antibody (e.g., an anti-C5 antibody) binds are also known in the art. For example, the binding epitope of an anti-C5 antibody can be identified by measuring the binding of the antibody to several (e.g., three, four, five, six, seven, eight, nine, 10, 15, 20, or 30 or more) overlapping peptide fragments of a complement component C5 protein (e.g., several overlapping fragments of a protein having the amino acid sequence depicted in any one of SEQ ID NOs:1-11). Each of the different overlapping peptides is then bound to a unique address on a solid support, e.g., separate wells of a multi-well assay plate. Next, the anti-C5 antibody is interrogated by contacting it to each of the peptides in the assay plate for an amount of time and under conditions that allow for the antibody to bind to its epitope. Unbound anti-C5 antibody is removed by washing each of the wells. Next, a detectably-labeled secondary antibody that binds to the anti-C5 antibody, if present in a well of the plate, is contacted to each of the wells, and unbound secondary antibody is removed by washing steps. The presence or amount of the detectable signal produced by the detectably-labeled secondary antibody in a well is an indication that the anti-C5 antibody binds to the particular peptide fragment associated with the well. See, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore chromatographic techniques (see, e.g., Pharmacia BIAtechnology Handbook, "Epitope Mapping," Section 6.3.2, (May 1994); and Johne et al. (1993) *J Immunol Methods* 160:20191-8).

The anti-C5 antibodies described herein can have activity in blocking the generation or activity of the C5a and/or C5b active fragments of a complement component C5 protein (e.g., a human C5 protein). Through this blocking effect, the anti-C5 antibodies inhibit, e.g., the proinflammatory effects of C5a and the generation of the C5b-9 membrane attack complex (MAC) at the surface of a cell. Anti-C5 antibodies that have the ability to block the generation of C5a are described in, e.g., Moongkarndi et al. (1982) *Immunobiol* 162:397 and Moongkarndi et al. (1983) *Immunobiol* 165:323.

In some embodiments, an anti-C5 antibody, or antigen-binding fragment thereof, can reduce the ability of a C5 protein to bind to human complement component C3b (e.g., C3b present in an AP or CP C5 convertase complex) by greater than 50 (e.g., greater than 55, 60, 65, 70, 75, 80, 85, 90, or 95 or more) %. In some embodiments, upon binding to a C5 protein, the anti-C5 antibody or antigen-binding fragment thereof can reduce the ability of the C5 protein to bind to complement component C4b (e.g., C4b present in a CP C5 convertase) by greater than 50 (e.g., greater than 55, 60, 65, 70, 75, 80, 85, 90, or 95 or more) %. Methods for determining whether an antibody can block the generation or activity of the C5a and/or C5b active fragments of a complement component C5 protein, or binding to complement component C4b or C3b, are known in the art and described in, e.g., U.S. Pat. No. 6,355,245 and Wurzner et al. (1991) *Complement Inflamm* 8:328-340.

In some embodiments, an anti-C5 antibody binds to an amino-terminal region of the alpha chain of a complement component C5 protein, but does not bind to free C5a. Epitopes for an anti-C5 antibody within the amino-terminal region of the alpha chain include, e.g., epitopes within the human sequence

VIDHQGTKSSKCVRQKVEGSS.    (SEQ ID NO: 5)

In some embodiments, the composition comprises, and/or the antibody is, eculizumab (Souris®; Alexion Pharmaceuticals®, Inc., Cheshire, CT). (See, e.g., Kaplan (2002) *Curr Opin Investig Drugs* 3(7):1017-23; Hill (2005) *Clin Adv Hematol Oncol* 3(11):849-50; and Rother et al. (2007) *Nature Biotechnology* 25(11): 1256-1488.)

In some embodiments, the composition comprises, and/or the antibody is, pexelizumab (Alexion Pharmaceuticals®, Inc., Cheshire, CT). See, e.g., Whiss (2002) *Curr Opin Investig Drugs* 3(6):870-7; Patel et al. (2005) *Drugs Today* (Barc) 41(3):165-70; and Thomas et al. (1996) *Mol Immunol* 33(17-18):1389-401.

In some embodiments, the C5 inhibitor is an antibody that binds to C5a (sometimes referred to herein as "an anti-C5a antibody"). In some embodiments, the antibody binds to C5a, but not to full-length C5. As discussed above, the proform of C5, a 1676 amino acid residue precursor protein, is processed by a series of proteolytic cleavage events. The first 18 peptides (numbered –18 to –1) constitute a signal peptide that is cleaved from the precursor protein. The remaining 1658 amino acid protein is cleaved in two places to form the alpha and beta chains. The first cleavage event occurs between amino acid residues 655 and 656. The second cleavage occurs between amino acid residues 659 to 660. The two cleavage events result in the formation of three distinct polypeptide fragments: (i) a fragment comprising amino acids 1 to 655, which is referred to as the beta chain; (ii) a fragment comprising amino acids 660 to 1658, which is referred to as the alpha chain; and (iii) a tetrapeptide fragment consisting of amino acids 656 to 659. The alpha chain and the beta chain polypeptide fragments are connected to each other via disulfide bond and constitute the mature C5 protein. The CP or AP C5 convertase activates mature C5 by cleaving the alpha chain between residues 733 and 734, which results in the liberation of C5a fragment (amino acids 660 to 733). The remaining portion of mature C5 is fragment C5b, which contains the residues 734 to 1658 of the alpha chain disulfide bonded to the beta chain.

In vivo, C5a is rapidly metabolized by a serum enzyme, carboxypeptidase B, to a 73 amino acid form termed "C5a des-Arg," which has lost the carboxyterminal arginine residue. Accordingly, in some embodiments, an antibody that binds to C5a also binds to desarginated C5a. In some embodiments, an antibody that binds to C5a does not bind to desarginated C5a.

In some embodiments, the C5 inhibitor is an antibody that binds to a neoepitope present in C5a, i.e., an epitope that becomes exposed upon the liberation of C5a from the alpha chain fragment of mature C5. Antibodies that bind to C5a (e.g., a neoepitope present in C5a) are known in the art as are methods for producing such antibodies. For example, an antibody that binds to C5a can have the binding specificity of a C5a neoepitope specific antibody described in any one of, e.g., PCT Publication No. WO 01/15731; Ames et al. (1994) *J Immunol* 152(9):4572-4581; Inoue (1989) *Complement Inflamm* 6(3):219-222; and U.S. Pat. No. 6,866,845. In another example, an antibody that binds to C5a can have the binding specificity of a commercial C5a neoepitope-specific antibody such as, but not limited to, sc-52633 (Santa Cruz Biotechnology, Inc., Santa Cruz, California),I152-1486 (BD Pharmingen/BD Biosciences), ab11877 (Abcam®, Cambridge, Massachusetts), and HM2079 (clone 2952; HyCult® Biotechnology, the Netherlands). In some embodiments, an antibody that binds to C5a can crossblock the binding of any of the aforementioned C5a neoepitope-specific antibodies.

In some embodiments, the C5 inhibitor can be an antibody that binds to a mammalian (e.g., human) C5a protein. For example, the antibody can bind to a human C5a protein having the following amino acid sequence: TLQKKIEE-IAAKYKHSVVKKCCYDGACVNNDET-CEQRAARISLGPRCIKAFTE CCVVASQLRANISHKDMQLGR (SEQ ID NO:12). The antibody can bind to human C5a at an epitope within or overlapping with the amino acid sequence: CCYD-GACVNNDETCEQRAAR (SEQ ID NO:13); KCCYD-GACVNNDETCEQR (SEQ ID NO:14); VNNDETCEQR (SEQ ID NO:15); VNNDET (SEQ ID NO:16); AARISLGPR (SEQ ID NO:17); CCYDGACVNNDETCEQRAA (SEQ ID NO:18); CCYDGACVNNDETCEQRA (SEQ ID NO:19); CCYDGACVNNDETCEQR (SEQ ID NO:20); CCYD-GACVNNDETCEQ (SEQ ID NO:21); CCYD-GACVNNDETCE (SEQ ID NO:22); CYDGACVNNDET-CEQRAAR (SEQ ID NO:23); YDGACVNNDETCEQRAAR (SEQ ID NO:24); or CYD-GACVNNDETCEQRAAR (SEQ ID NO:25). In some embodiments, an antibody can bind to a human C5a protein or fragment thereof containing an amino acid sequence that contains, or consists of, at least four (e.g., at least four, five, six, seven, eight, nine, 10, 11, 12, 13, 14, 15, 16, or 17 or more) consecutive amino acids depicted in any one of SEQ ID NOs:12-25. Additional C5a protein fragments to which an antibody described herein can bind and methods for generating suitable C5a-specific antigen combining sites are set forth in, e.g., U.S. Pat. No. 4,686,100, the disclosure of which is incorporated herein by reference in its entirety.

In some embodiments, the binding of an antibody to C5a can inhibit the biological activity of C5a. Methods for measuring C5a activity include, e.g., chemotaxis assays, RIAs, or ELISAs (see, e.g., Ward and Zvaifler (1971) *J Clin Invest* 50(3):606-16 and Wurzner et al. (1991) *Complement Inflamm* 8:328-340). In some embodiments, the binding of an antibody to C5a can inhibit the interaction between C5a and C5aR1. Suitable methods for detecting and/or measuring the interaction between C5a and C5aR1 (in the presence and absence of an antibody) are known in the art and described in, e.g., Mary and Boulay (1993) *Eur J Haematol* 51(5):282-287; Kaneko et al. (1995) *Immunology* 86(1):149-154; Giannini et al. (1995) *J Biol Chem* 270(32):19166-19172; and U.S. Patent Application Publication No. 20060160726. For example, the binding of detectably labeled (e.g., radioactively labeled) C5a to C5aR1-expressing peripheral blood mononuclear cells can be evaluated in the presence and absence of an antibody. A decrease in the amount of detectably-labeled C5a that binds to C5aR1 in the presence of the antibody, as compared to the amount of binding in the absence of the antibody, is an indication that the antibody inhibits the interaction between C5a and C5aR1. In some embodiments, the binding of an antibody to C5a can inhibit the interaction between C5a and C5L2 (see below). Methods for detecting and/or measuring the interaction between C5a and C5L2 are known in the art and described in, e.g., Ward (2009) *J Mol Med* 87(4):375-378 and Chen et al. (2007) *Nature* 446(7132): 203-207 (see below).

In some embodiments, the C5 inhibitor is an antibody that binds to C5b (sometimes referred to herein as "an anti-C5b antibody"). In some embodiments, the antibody binds to C5b, but does not bind to full-length C5. The structure of C5b is described above and also detailed in, e.g., Müller-Eberhard (1985) *Biochem Soc Symp* 50:235-246; Yamamoto and Gewurz (1978) *J Immunol* 120(6):2008-2015; and Haviland et al. (1991), supra. As described above, C5b combines with C6, C7, and C8 to form the C5b-8 complex at the surface of the target cell. Protein complex intermediates formed during the series of combinations include C5b-6 (including C5b and C6), C5b-7 (including C5b, C6, and C7), and C5b-8 (including C5b, C6, C7, and C8). Upon binding of several C9 molecules, the membrane attack complex (MAC, C5b-9 terminal complement complex (TCC)) is formed. When sufficient numbers of MACs insert into target cell membranes, the openings they create (MAC pores) mediate rapid osmotic lysis of the target cells.

In some embodiments, the binding of an antibody to C5b can inhibit the interaction between C5b and C6. In some embodiments, the binding of the antibody to C5b can inhibit the assembly or activity of the C5b-9 MAC-TCC. In some embodiments, the binding of an antibody to C5b can inhibit complement-dependent cell lysis (e.g., in vitro and/or in vivo). Suitable methods for evaluating whether an antibody inhibits complement-dependent lysis include, e.g., hemolytic assays or other functional assays for detecting the activity of soluble C5b-9. For example, a reduction in the cell-lysing ability of complement in the presence of an antibody can be measured by a hemolysis assay described by Kabat and Mayer (eds.), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) *N Engl J Med* 350(6):552.

Antibodies that bind to C5b as well as methods for making such antibodies are known in the art. See, e.g., U.S. Pat. No. 6,355,245. Commercially available anti-C5b antibodies are available from a number of vendors including, e.g., Hycult® Biotechnology (catalogue number: HM2080; clone 568) and Abcam® (ab46151 or ab46168).

In some embodiments, the C5 inhibitor is an antibody that binds to a mammalian (e.g., human) form of C5b. For example, the antibody can bind to a portion of a human C5b protein having the following amino acid sequence: QEQ-TYVISAPKIFRVGAS-ENIVIQVYGYTEAFDATISIKSYPDKKFSYSSGHVHL SSENKFQNSAILTIQPKQLPGGQN-PVSYVYLEVVSKHFSKSKRMPITYDNGFLF IHTDK-PVYTPDQSVKVRVYSLNDDLKPAKRETV-LTFIDPEGSEVDMVEEIDHI GIISFPDFKIPSNPRYGMW-TIKAKYKEDFSTTGTAYFEVKEYVLPHFSVSIEPEY NFIGYKNFKNFEITIKARYFYNKV-VTEADVYITFGIREDLKDDQKEMMQTAM QNTMLIN-GIAQVTFDSETAVKELSYYSLEDLNNKY-LYIAVTVIESTGGFSEEAE IPGIKYVLSPYKLNLVATPLFLKP- GIPYPIKVQVKDSLDQLVGGVPVILNAQTID VNQETS-DLDPSKSVTRVDDGVASFVLNLPSGVTV-LEFNVKTDAPDLPEENQA REGYRAIAYSSLSQYLYIDWTDNH-KALLVGEHLNIIVTPKSPYIDKITHYNYL ILSKGKIIH-FGTREKFSDASYQSINIPVTQNMVPSSR-LLVYYIVTGEQTAELVSD SVWLNIEEKCGNQLQVHLSPDADAY-SPGQTVSLNMATGMDSWVALAAVDS AVYGVQR-GAKKPLERVFQFLEKSDLGCGAGGGLN-NANVFHLAGLTFLTNAN ADDSQENDEPCKEIL (SEQ ID NO:4). In some embodiments, the antibody can bind to a portion of a human C5b protein having the following amino acid sequence: LHMKTLLPVSKPEIRSYFPESWLW-EVHLVPRRKQLQFALPDSLTTWEIQGIGIS NTGIC-VADTVKAKVFKDVFLEMNIPYSVVRGE-QIQLKGTVYNYRTSGMQFCV KMSAVEGICT-SESPVIDHQGTKSSKCVRQKVEG-SSSHLVTFTVLPLEIGLHNIN FSLETWFGKEILVKTL-RVVPEGVKRESYSGVTLDPRGIYGTISRRKEFPYRIPL DLVPKTEIKRILSVKGLLVGEILSAV-LSQEGINILTHLPKGSAEAELMSVVPVFY VFHYLET-GNHWNIFHSDPLIEKQKLKKKLKEGML-SIMSYRNADYSYSVWKG GSASTWLTAFALRVLGQVNKYVEQNQN-SICNSLLWLVENYQLDNGSFKENS QYQPIKLQGTLPVEARENSLYLTAFTVI-GIRKAFDICPLVKIDTALIKADNFLLE NTLPAQSTFT-LAISAYALSLGDKTHPQFRSIVSALKRE-ALVKGNPPIYRFWKD NLQHKDSSVPNTGTARMVETTAY-ALLTSLNLKDINYVNPVIKWLSEEQRYGG GFYSTQD-TINAIEGLTEYSLLVKQLRLSMDID-VSYKHKGALHNYKMTDKNFL GRPVEVLLNDDLIVSTGFGSGLATVHVT-TVVHKTSTSEEVCSFYLKIDTQDIEA SHYRGYGNS-DYKRIVACASYKPSREESSSGSSHAVM-DISLPTGISANEEDLKA LVEGVDQLFTDYQIKDGHVILQLNSIPSS DFLCVR-FRIFELFEVGFLSPATFTVYEYHRPD-KQCTMFYSTSNIKIQKVCEGAA CKCVEADCGQM-QEELDLTISAETRKQTACKPEIAYAYKVSITSITVENV-FVKY KATLLDIYKTGEAVAEKDSEIT-FIKKVTCTNAELVKGRQYLIMGKEALQIKYN FSFRY-IYPLDSLTWIEYWPRDTTCSSC-QAFLANLDEFAEDIFLNGC (SEQ ID NO:26). In some embodiments, the antibody can bind to human C5b protein or fragment thereof containing an amino acid sequence that contains, or consists of, at least four (e.g., at least four, five, six, seven, eight, nine, 10, 11, 12, 13, 14, 15, 16, 17, 18, 19, or 20 or more) consecutive amino acids depicted in SEQ ID NO:4 or SEQ ID NO:26.

Additional exemplary sub-fragments of human C5b or C5a to which a C5 inhibitor antibody can bind are disclosed in, e.g., U.S. Pat. No. 6,355,245, the disclosure of which is incorporated herein by reference.

In some embodiments, the inhibitor is an antibody that specifically binds to a C5a polypeptide (e.g., the human C5a polypeptide having the amino acid sequence depicted in SEQ ID NO:12). In some embodiments, the inhibitor is an antibody that specifically binds to a C5b polypeptide.

Methods for determining whether a particular agent is an inhibitor of human complement component C5 are described herein and are known in the art. For example, the concentration and/or physiologic activity of C5a and C5b in a body fluid can be measured by methods well known in the art. Methods for measuring C5a concentration or activity include, e.g., chemotaxis assays, RIAs, or ELISAs (see, e.g., Ward and Zvaifler (1971) *J Clin Invest* 50(3):606-16 and Wurzner et al. (1991) *Complement Inflamm* 8:328-340). For C5b, hemolytic assays or assays for soluble C5b-9 as discussed herein can be used. Other assays known in the art can also be used. Using assays of these or other suitable types, candidate agents capable of inhibiting human complement component C5 such as an anti-C5 antibody, can be screened in order to, e.g., identify compounds that are useful in the methods described herein and determine the appropriate dosage levels of such compounds.

Methods for detecting inhibition of expression of mRNA or protein (e.g., inhibition of human C5 protein expression or expression of an mRNA encoding human C5 protein) are well known in the art of molecular biology and include, e.g., Northern blot and RT-PCR (or quantitative RT-PCR) techniques for mRNA and for protein detection, Western blot, dot blot, or ELISA techniques. See, e.g., Sambrook et al. (1989) "Molecular Cloning: A Laboratory Manual, $2^{nd}$ Edition," Cold Spring Harbor Laboratory Press, Cold Spring Harbor, N.Y.

Methods for determining whether a candidate compound inhibits the cleavage of human C5 into forms C5a and C5b are known in the art and described in, e.g., Moongkarndi et al. (1982) *Immunobiol* 162:397; Moongkarndi et al. (1983) *Immunobiol* 165:323; Isenman et al. (1980) *J Immunol* 124(1):326-31; Thomas et al. (1996) *Mol Immunol* 33(17-18):1389-401; and Evans et al. (1995) *Mol Immunol* 32(16):1183-95.

Inhibition of human complement component C5 can also reduce the cell-lysing ability of complement in a subject's body fluids. Such reductions of the cell-lysing ability of complement present can be measured by methods well known in the art such as, for example, by a conventional hemolytic assay such as the hemolysis assay described by Kabat and Mayer (eds), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) *N Engl J Med* 350(6):552.

In some embodiments, the compositions described herein can contain an inhibitor of interferon alpha. Any compound which binds to or otherwise blocks the generation and/or activity of interferon alpha may be utilized in accordance with the present disclosure. For example, an inhibitor of interferon alpha can be, e.g., a small molecule, a nucleic acid or nucleic acid analog (e.g., an siRNA, a dsRNA, a ribozyme, a triple-helix former, an aptamer), a peptidomimetic, or a macromolecule that is not a nucleic acid or a protein. These agents include, but are not limited to, small organic molecules, RNA aptamers, L-RNA aptamers, Spiegelmers, antisense compounds, double stranded RNA, small interfering RNA, locked nucleic acid inhibitors, and peptide nucleic acid inhibitors. In some embodiments, an inhibitor of interferon alpha may be a protein or protein fragment. In some embodiments, the inhibitor of interferon alpha is an inhibitor of the receptor (interferon alpha receptor) to which interferon alpha binds. The human interferon alpha receptor is described in, e.g., Novick et al. (1994) *Cell* 77(3):391-400; Chill et al. (2003) *Structure* 11(7):791-802; and Uzé et al. (2007) *Curr Top Microbiol Immunol* 316:71-95. In some embodiments, the inhibitor of interferon alpha binds to interferon alpha or its receptor and inhibits the interaction between interferon alpha and its receptor.

In some embodiments, the inhibitor of interferon alpha is an antibody, or antigen-binding fragment thereof, which binds to an interferon alpha protein. (Hereinafter, the antibody may sometimes be referred to as an "anti-interferon alpha antibody.") Exemplary anti-interferon alpha antibodies are known in the art and described in, e.g., U.S. patent application publication nos. 20090324605, 20070059309, and 20080160030; U.S. Pat. Nos. 7,087,726 and 4,423,147, the disclosures of each of which are incorporated herein by reference in their entirety.

Additional exemplary anti-interferon alpha antibodies that can be used in the compositions and methods described herein include, e.g., MEDI-545 (MDX-1103; AstraZeneca®/Medimmune®).

Methods for Producing an Antibody

Suitable methods for producing an antibody (e.g., an anti-C5 antibody or an anti-interferon alpha antibody), or antigen-binding fragments thereof, in accordance with the disclosure are known in the art (see, e.g., U.S. Pat. No. 6,355,245) and described herein. For example, monoclonal anti-C5 antibodies may be generated using complement component C5-expressing cells, a C5 polypeptide, or an antigenic fragment of C5 polypeptide, as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to human complement component C5. Similarly, monoclonal anti-interferon alpha antibodies may be generated using an interferon alpha polypeptide, or an antigenic fragment of interferon alpha polypeptide, as an immunogen, thus raising an immune response in animals from which antibody-producing cells and in turn monoclonal antibodies may be isolated.

Moreover, antibodies derived from recombinant libraries ("phage antibodies") may be selected using antigenic polypeptides such as a complement component protein or interferon alpha, as bait to isolate the antibodies or polypeptides on the basis of target specificity. The production and isolation of non-human and chimeric antibodies are well within the purview of the skilled artisan.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See, U.S. Pat. Nos. 5,225,539 and 7,393,648, the contents of each of which are incorporated herein by reference.

Antibodies can be obtained from animal serum or, in the case of monoclonal antibodies or fragments thereof, produced in cell culture. Recombinant DNA technology can be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g., E. coli or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic (e.g., bicistronic) DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like).

Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2xYT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) *Nature* 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, e.g.: WO97/08320; U.S. Pat. No. 5,427,908; U.S. Pat. No. 5,508,717; Smith (1985) *Science* 225:1315-1317; Parmley and Smith (1988) *Gene* 73:305-318; De La Cruz et al. (1988) *Journal of Biological Chemistry* 263:4318-4322; U.S. Pat. No. 5,403,484; U.S. Pat. No. 5,223,409; WO88/06630; WO92/15679; U.S. Pat. No. 5,780,279; U.S. Pat. No. 5,571,698; U.S. Pat. No. 6,040,136; Davis et al. (1999) *Cancer Metastasis Rev* 18(4):421-5; and Taylor et al. (1992) *Nucleic Acids Research* 20: 6287-6295; Tomizuka et al. (2000) *Proc Natl Acad Sci USA* 97(2): 722-727, the contents of each of which are incorporated herein by reference in their entirety.

The cell culture supernatants are screened for the desired antibodies by, e.g., immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a complement component C5-expressing cell line, or with Protein-A or -G.

Another embodiment provides a process for the preparation of a bacterial cell line secreting antibodies directed against a protein (e.g., a complement protein or interferon alpha) in a suitable mammal. A phage display library produced from the immunized rabbit is constructed and panned for the desired antibodies in accordance with methods well known in the art (such as, e.g., the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against a protein of interest (e.g., C5 protein or interferon alpha). In that process, a suitable mammal, for example a Balb/c mouse, is immunized with one or more polypeptide antigens of interest or antigenic fragments thereof. Antibody-producing cells of the immunized mammal are grown briefly in culture or fused with cells of a suitable myeloma cell line. The hybrid cells obtained in the fusion are cloned, and cell clones secreting the desired antibodies are selected. Methods for preparing a hybridoma cell line include immunizing Balb/c mice by injecting subcutaneously and/or intraperitoneally an immunogenic composition containing the protein of interest (or an immunogenic fragment thereof) several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application (e.g., methods for treating or preventing Degos' disease in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. See, e.g., Jakobovits et al. (1993) *Proc Natl Acad Sci USA* 90:2551; Jakobovits et al. (1993) *Nature* 362:255-258; Bruggemann et al. (1993) *Year in Immunol* 7:33; and Duchosal et al. (1992) *Nature* 355:258. Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al. (1991) *J Mol Biol* 227: 381; Marks et al. (1991) *J Mol Biol,* 222:581-597; and Vaughan et al. (1996) *Nature Biotech* 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132, 6,680,209, 4,634,666, and Ostberg et al. (1983), *Hybridoma* 2:361-367, the contents of each of which are incorporated herein by reference in their entirety.

For the generation of human antibodies, also see Mendez et al. (1998) *Nature Genetics* 15:146-156 and Green and Jakobovits (1998) *J Exp Med* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Publication Nos. 2003-0229905 A1, 2004-0010810 A1, US 2004-0093622 A1, 2006-0040363 A1, 2005-0054055 A1, 2005-0076395 A1, 2005-0287630 A1. See also International Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; and 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Application Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res* 20: 6287; Chen et al. (1993) *Int. Immunol.* 5: 647; Tuaillon et al. (1993) *Proc Natl Acad Sci USA* 90: 3720-4; Choi et al. (1993) *Nature Genetics* 4: 117; Lonberg et al. (1994) *Nature* 368: 856-859; Taylor et al. (1994) *International Immunology* 6: 579-591; Tuaillon et al. (1995) *J Immunol* 154: 6453-65; Fishwild et al. (1996) *Nature Biotechnology* 14: 845; and Tuaillon et al. (2000) *Eur J Immunol.* 10: 2998-3005, the disclosures of each of which are hereby incorporated by reference in their entirety.

In certain embodiments, de-immunized antibodies or antigen-binding fragments thereof are provided. De-immunized antibodies or antigen-binding fragments thereof are antibodies that have been modified so as to render the antibody or antigen-binding fragment thereof non-immunogenic, or less immunogenic, to a given species (e.g., to a human). De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In some embodiments, a recombinant DNA comprising an insert coding for a heavy chain variable domain and/or for a light chain variable domain of an antibody (e.g., an anti-C5 antibody or an anti-interferon alpha antibody) is produced and transfected into a host cell for expression of the antibody. The term DNA includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of anti-C5 antibodies can be enzymatically or chemically synthesized to contain the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods well known in the art.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-C5 antibody or antigen-binding fragment (e.g., Fab, Fv, single-chain scFv, Fab', and F(ab')$_2$) is linked to a molecule that increases the half-life of the antibody or antigen-binding fragment (see above).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA*, 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA*, 79:7147), polyoma virus (Deans et al. (1984) *Proc Natl Acad Sci USA* 81:1292), or SV40 virus (Lusky and Botchan (1981) *Nature* 293:79).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983) *Mol Cell Biol* 3:280; Cepko et al. (1984) *Cell* 37:1053; and Kaufman (1985) *Proc Natl Acad Sci USA* 82:689.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for a human complement protein or interferon alpha protein, and the other one is for any other antigen.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) *Nature* 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods in Enzymology* 121:210; PCT Publication No. WO 96/27011; Brennan et al. (1985) *Science* 229:81; Shalaby et al., J Exp Med (1992) 175:217-225; Kostelny et al. (1992) *J Immunol* 148(5):1547-1553; Hollinger et al. (1993) *Proc Natl Acad Sci USA* 90:6444-6448; Gruber et al. (1994) *J Immunol* 152:5368; and Tutt et al. (1991) *J Immunol* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368. Alternatively, the antibodies can be "linear antibodies" as described in, e.g., Zapata et al. (1995) *Protein Eng.* 8(10):1057-1062. Briefly, these antibodies comprise a pair of tandem Fd segments ($V_H$-$C_H$1-$V_H$-$C_H$1) which form a pair of antigen binding regions. Linear antibodies can be bispecific or monospecific.

The disclosure also embraces variant forms of bispecific antibodies such as the tetravalent dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024,188 and WO 07/024,715, the disclosures of each of which are incorporated herein by reference in their entirety.

Pharmaceutical Compositions and Formulations

The compositions containing a complement inhibitor (e.g., an inhibitor of human complement component C5 such as an anti-C5 antibody or antigen-binding fragment thereof or an inhibitor of interferon alpha) can be formulated as a pharmaceutical composition, e.g., for administration to a subject to treat Degos' disease. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. In some embodiments, a composition can be formulated for storage at a temperature below 0° C. (e.g., −20° C. or −80° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing an anti-C5 antibody intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating an antibody described herein in the required amount in an appropriate solvent with one or a combination of ingredients enumerated above, as required, followed by filter sterilization. Generally, dispersions are prepared by incorporating an inhibitor of human complement (e.g., an anti-C5 antibody) and/or an inhibitor of interferon alpha described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of the antibody described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts and gelatin.

In certain embodiments, the complement inhibitor (e.g., an anti-C5 antibody or antigen-binding fragment thereof) or inhibitor of interferon alpha can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, an inhibitor described herein can be formulated in a composition suitable for intrapulmonary administration (e.g., for administration via nebulizer) to a mammal such as a human. Methods for preparing such compositions are well known in the art and described in, e.g., U.S. Patent Application Publication No. 20080202513; U.S. Pat. Nos. 7,112,341 and 6,019,968; and PCT Publication Nos. WO 00/061178 and WO 06/122257, the disclosures of each of which are incorporated herein by reference in their entirety. Dry powder inhaler formulations and suitable systems for administration of the formulations are described in, e.g., U.S. Patent Application Publication No. 20070235029, PCT Publication No. WO 00/69887; and U.S. Pat. No. 5,997,848.

In some embodiments, an inhibitor of human complement (e.g., an anti-C5 antibody or antigen-binding fragment thereof) or inhibitor of interferon alpha described herein can be modified, e.g., with a moiety that improves its stabilization and/or retention in circulation, e.g., in blood, serum, or other tissues. The stabilization moiety can improve the stability, or retention of, the antibody by at least 1.5 (e.g., at least 2, 5, 10, 15, 20, 25, 30, 40, or 50 or more) fold.

The nucleic acid inhibitors of human complement described herein (e.g., an anti-sense nucleic acid or siRNA)

can be incorporated into a gene construct to be used as a part of a gene therapy protocol to deliver nucleic acids that can be used to express and produce agents within cells. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin®) or derivatized (e.g., antibody conjugated), polylysine conjugates, gramicidin S, artificial viral envelopes or other such intracellular carriers, as well as direct injection of the gene construct or $CaPO_4$ precipitation carried out in vivo. (See also, "Ex vivo Approaches," below.) Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc Natl Acad Sci USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immunol* 150:4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5D1324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and McLaughlin et al. (1989) *J Virol* 62:1963-1973.

In some embodiments, more than one (e.g., two, three, four, five, six, seven, eight, nine, or 10 or more) inhibitor(s) (e.g., one or more inhibitors of human C5) can be co-formulated. For example, a C5-specific siRNA and an anti-C5 antibody can be formulated together.

In some embodiments, an inhibitor of human complement (e.g., an inhibitor of human complement such as an anti-C5 antibody or antigen-binding fragment thereof) or inhibitor of interferon alpha described herein can be formulated with one or more additional active agents useful for treating Degos' disease or ameliorating a symptom thereof. For example, an anti-C5 antibody can be formulated with an immunosuppressive agent. Immunosuppressive agents include, e.g., corticosteroids, phenylbutazone, azathioprine, methotrexate, cyclosporine, tacrolimus, and mycophenolate mofetil, cyclophosphamide, and an anti-CD20 agent such as rituximab (Rituxan™; Biogen Idec®, Cambridge, MA). In some embodiments, the inhibitor human complement can be formulated for administration to a subject along with intravenous immunoglobulin therapy (IVIG), red cell transfusion, plasmapheresis, or with plasma exchange. See, e.g., Dyrsen et al. (2008), supra and Zhu et al. (2007), supra.

In some embodiments, the inhibitor of human complement can be formulated for joint therapy (e.g., simultaneous or concurrent) with an antithrombotic agent and/or an anticoagulant such as, but not limited to, clopidogrel, aspirin, dipyridamole, warfarin (Coumadin), heparin, phenindione, fondaparinux, idraparinux, and thrombin inhibitors (e.g., argatroban, lepirudin, bivalirudin, or dabigatran). An inhibitor of human complement (e.g., an anti-C5 antibody) can also be formulated for use with a fibrinolytic agent (e.g., ancrod, $\epsilon$-aminocaproic acid, antiplasmin-$a_1$, prostacyclin, and defibrotide) for the treatment of Degos' disease.

In some embodiments, e.g., where the Degos' disease is associated with an infection, the inhibitor human complement and/or inhibitor of interferon alpha can be formulated with one or more agents for use in treating an infection. For example, a C5 inhibitor can be formulated with an antibiotic or an anti-viral agent.

When the inhibitor of human complement is to be used in combination with a second active agent, or when two or more inhibitors of human complement are to be used (e.g., an anti-C5 antibody and an anti-factor B antibody), the agents can be formulated separately or together. For example, the respective pharmaceutical compositions can be mixed, e.g., just prior to administration, and administered together or can be administered separately, e.g., at the same or different times (see below).

Likewise, when the inhibitor of interferon alpha (e.g., an anti-interferon alpha antibody) is to be used in combination with a second active agent, or when two or more inhibitors of interferon alpha are to be used, the agents can be formulated separately or together.

As described above, a composition can be formulated such that it includes a therapeutically effective amount of an inhibitor of human complement (e.g., an anti-C5 antibody or antigen-binding fragment thereof) or the composition can be formulated to include a sub-therapeutic amount of the inhibitor and a sub-therapeutic amount of one or more additional active agents such that the components in total are therapeutically effective for treating Degos' disease. In some embodiments, a composition can be formulated to include two or more inhibitors of human complement, each at sub-therapeutic doses, such that the inhibitors in total are at a concentration that is therapeutically effective for treating Degos' disease. A composition can be formulated such that it includes a therapeutically effective amount of an inhibitor of interferon alpha (e.g., an anti-interferon alpha antibody or antigen-binding fragment thereof) or the composition can be formulated to include a sub-therapeutic amount of the inhibitor and a sub-therapeutic amount of one or more additional active agents such that the components in total are therapeutically effective for treating Degos' disease. In some embodiments, a composition can be formulated to include two or more inhibitors of interferon alpha, each at sub-therapeutic doses, such that the inhibitors in total are at a concentration that is therapeutically effective for treating Degos' disease. In some embodiments, the composition includes an inhibitor of human complement and an inhibitor of interferon alpha. Methods for determining a therapeutically effective dose (e.g., a therapeutically effective dose of an anti-C5 antibody or an anti-interferon antibody) are known in the art and described herein.

Methods for Treatment

The above-described compositions are useful in, inter alia, methods for treating or preventing Degos' disease in a subject (e.g., a human). The compositions can be administered to a subject, e.g., a human subject, using a variety of methods that depend, in part, on the route of administration. The route can be, e.g., intravenous injection or infusion (IV), subcutaneous injection (SC), intraperitoneal (IP), or intramuscular injection.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. (See, e.g., U.S. Patent Publication No. 20080241223; U.S. Pat. Nos. 5,501,856; 4,863,457; and 3,710,795; EP488401; and EP 430539, the disclosures of each of which are incorporated herein by reference in their entirety.) The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

A suitable dose of an inhibitor of human complement (e.g., an anti-C5 antibody or fragment thereof) or an inhibitor of interferon alpha (e.g., an anti-interferon alpha antibody), which dose is capable of treating or preventing Degos' disease in a subject, can depend on a variety of factors including, e.g., the age, sex, and weight of a subject to be treated and the particular inhibitor compound used. For example, a different dose of a siRNA specific for human C5 may be required to treat a subject with Degos' disease as compared to the dose of an anti-C5 antibody required to treat the same patient. Other factors affecting the dose administered to the subject include, e.g., the type or severity of Degos' disease. For example, a subject having a cutaneous form of Degos' disease may require administration of a different dosage of the inhibitor than a subject with a systemic form of Degos' disease. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner (e.g., doctor or nurse).

The inhibitor can be administered as a fixed dose, or in a milligram per kilogram (mg/kg) dose. In some embodiments, the dose can also be chosen to reduce or avoid production of antibodies or other host immune responses against one or more active agents in the composition. While in no way intended to be limiting, exemplary dosages of a complement inhibitor (e.g., an anti-C5 antibody) and/or an inhibitor of interferon alpha include, e.g., 1-100 µg/kg, 0.5-50 µg/kg, 0.1-100 µg/kg, 0.5-25 µg/kg, 1-20 µg/kg, and 1-10 µg/kg, 1-100 mg/kg, 0.5-50 mg/kg, 0.1-100 mg/kg, 0.5-25 mg/kg, 1-20 mg/kg, and 1-10 mg/kg. Exemplary dosages of an antibody described herein include, without limitation, 0.1 µg/kg, 0.5 µg/kg, 1.0 µg/kg, 2.0 µg/kg, 4 µg/kg, and 8 µg/kg, 0.1 mg/kg, 0.5 mg/kg, 1.0 mg/kg, 2.0 mg/kg, 4 mg/kg, and 8 mg/kg.

In some embodiments, a human can be intravenously administered an anti-C5 antibody (e.g., eculizumab) at a dose of about 900 mg about every 12 (e.g., about every 10, 11, 13, 14, 15, 16, 17, 18, 19, 20, 21, 28, 30, 42, or 49 or more) days. See, e.g., Hill et al. (2005) *Blood* 106(7):2559.

In some embodiments, a human can be intravenously administered an anti-C5 antibody (e.g., eculizumab) at a dose of about 600 (e.g., about 625, 650, 700, 725, 750, 800, 825, 850, 875, 900, 925, 950, or 1,000 or more) mg every week, optionally, for two or more (e.g., three, four, five, six, seven, or eight or more) weeks. Following the initial treatment, the human can be administered the antibody at a dose of about 900 mg about every 14 (e.g., about every 15, 16, 17, 18, 19, 20, 21, 28, 30, 42, or 49 or more) days, e.g., as a maintenance dose. See, e.g., Hillmen et al. (2004) *N Engl J Med.* 350(6): 552-9 and Dmytrijuk et al. (2008) *The Oncologist* 13(9):993.

A pharmaceutical composition can include a therapeutically effective amount of an inhibitor of human complement component C5 (e.g., an anti-C5 antibody or antigen-binding fragment thereof) and/or a therapeutically effective amount of an inhibitor of interferon alpha. Such effective amounts can be readily determined by one of ordinary skill in the art based, in part, on the effect of the administered inhibitor, or the combinatorial effect of the antibody and one or more additional active agents, if more than one agent is used. A therapeutically effective amount of an inhibitor of human complement (e.g., an anti-C5 antibody) can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of Degos' disease. For example, a therapeutically effective amount of an inhibitor of human complement (e.g., an anti-C5 antibody) can inhibit (lessen the severity of or eliminate the occurrence of) and/or prevent Degos' disease, and/or any one of the symptoms of Degos' disease known in the art or described herein. A therapeutically effective amount is also one in which any toxic or detrimental effects of the composition are outweighed by the therapeutically beneficial effects.

The terms "therapeutically effective amount" or "therapeutically effective dose," or similar terms used herein are intended to mean an amount of an agent (e.g., an inhibitor of human complement) that will elicit the desired biological or medical response (e.g., an improvement in one or more symptoms of Degos' disease). In some embodiments, a composition described herein contains a therapeutically effective amount of an inhibitor of human complement component C5. In some embodiments, a composition described herein contains a therapeutically effective amount of an antibody, or antigen-binding fragment thereof, which binds to a complement component C5 protein. In some embodiments, the composition contains two or more (e.g., three, four, five, six, seven, eight, nine, 10, or 11 or more) different inhibitors of human complement such that the composition as a whole is therapeutically effective. For example, a composition can contain an antibody that binds to a human C5 protein and a siRNA that binds to, and promotes the degradation of, an mRNA encoding a human C5 protein, wherein the antibody and siRNA are each at a concentration that when combined are therapeutically effective. In some embodiments, the composition contains the inhibitor and one or more second active agents such that the composition as a whole is therapeutically effective. For example, the composition can contain an antibody that binds to a human C5 protein and another agent useful for treating or preventing Degos' disease.

In some embodiments, a composition described herein contains a therapeutically effective amount of an anti-inteferon alpha antibody or an antigen-binding fragment thereof.

Toxicity and therapeutic efficacy of such compositions can be determined by known pharmaceutical procedures in cell cultures or experimental animals. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions, or complement inhibitors (e.g., anti-C5 antibodies) of the compositions, that exhibit high therapeutic indices are preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such inhibitors lies generally within a range of circulating concentrations of the inhibitor(s) (e.g., an anti-C5 antibody, an anti-interferon alpha antibody, or antigen-binding fragments thereof) that include the $ED_{50}$ with little or no toxicity. The dosage may vary within this range depending upon the dosage form employed and the route of administration utilized. For an inhibitor of human complement component C5 (e.g., an anti-C5 antibody) used as described herein (e.g., for treating or preventing Degos' disease), the therapeutically effective dose can be estimated initially from cell culture assays. Levels of the complement inhibitor in, e.g., the plasma of treated humans or animals may be measured, for example, by high performance liquid chromatography.

In some embodiments, the required dose of an inhibitor of human complement (e.g., an anti-C5 antibody) can be determined based on the concentration in the subject's blood of the complement protein to which the inhibitor is directed. For example, a subject having a higher concentration of circulating human C5 protein levels may require a higher dose of a human C5 inhibitor than a subject having lower levels of circulating human C5. Methods for determining the concentration of human complement in a blood-derived fluid sample from a subject are known in the art. For example, a method for determining serum C5 levels is described in, e.g., Rawal et al. (1998) *J Biol Chem* 273(27):16828-16835.

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

In some embodiments, the subject is one who is refractory to one or more additional therapeutic agents that were administered to treat Degos' disease. "Resistance" to a therapy, "refractory" to therapy, and like grammatical phrases, as used herein, refer to a patient's clinical state of being, in which there is a reduction in the effectiveness of a given therapy in treating or curing a given disorder (e.g., Degos' disease) or a reduction in the effectiveness of the treatment in ameliorating one or more symptoms associated with the disorder. For example, the therapeutic benefits of IVIg to a patient afflicted with Degos' disease may diminish over time such that the disease remains or progresses even with IVIg therapy. See, e.g., De Breucker et al. (2008), supra.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an inhibitor of human complement or an inhibitor of interferon alpha).

As used herein, a subject "at risk for developing Degos' disease" is a subject having one or more (e.g., two, three, four, five, six, seven, or eight or more) risk factors for developing the disorder. Risk factors for Degos' disease are well known in the art of medicine and include, e.g., a predisposition to develop the condition, i.e., a family history of the condition or a genetic status associated with Degos' disease such as, e.g., a Protein S deficiency. See, e.g., Gileberte et al. (2005) *Br J Dermatol* 153(3):666-7. Risk factors for Degos' disease also include those conditions that are associated with Degos' disease such as, but not limited to, viral infections (e.g., HIV or B19 parvovirus infections), a procoagulant state (e.g., Factor V Leiden), or an autoimmune disease such as LE, dermatomyositis, scleroderma, and antiphospholipid syndrome. Hereinafter, such manifestations of Degos' disease may be, where appropriate, referred to as, e.g., "infection-associated Degos' disease" or "autoimmune-associated Degos' disease." From the above it will be clear that subjects "at risk for developing Degos' disease" are not all the subjects within a species of interest.

A subject "suspected of having Degos' disease" is one having one or more (e.g., two, three, four, five, six, seven, eight, nine, or 10 or more) symptoms of the condition. Symptoms of this condition are known to those of skill in the art of medicine and include, e.g., skin lesions (e.g., one or more papules that are raised and skin- or rose-colored, which papules progress to depressed scars with white centers and surrounding erythema and telangiectasias), gastrointestinal bleeding, vomiting, enterocutaneous fistula, neurological symptoms (e.g., facial and acral paraesthesia, headaches, dizziness, aphagia, paraplegia, gaze palsy, epilepsy, memory loss, or altered sensation), strokes, diplopia, ptosis, visual-field defects, weakness, shortness of breath, and chest pain. In some embodiments, Degos' disease is associated with the presence in the patients of anticardiolipin antibodies, the lupus anticoagulant, antiphospholipid antibodies, or vascular IgA deposition. See, e.g., Englert et al. (1984), supra; Crowson et al. (2002), supra; and Grattan and Burton (1991) *Semin Dermatol* 10(3):152-159. From the above it will be clear that subjects "suspected of having Degos' disease" are not all the subjects within a species of interest.

In some embodiments, the methods can include identifying the subject as one having, suspected of having, or at risk for developing, Degos' disease. Suitable methods for identifying the subject are known in the art. For example, Ackerman describes a histological method for positively identifying a Degos' disease-associated cutaneous lesion. *Am J Dermatopathol* (1985) 7(2):105-7. As described above, Degos' disease can be associated with the presence in the patients of anticardiolipin antibodies, the lupus anticoagulant, and/or antiphospholipid antibodies. Diagnostic histological methods are also exemplified in the working examples. Suitable methods for detecting the presence of these antibodies in the blood of a patient are known in the art and described in, e.g., Caux et al. (1994) *Ann Dermatol Venereol* 121:537-542. In some embodiments, Degos' disease can be associated with IgA deposition within the cutaneous vasculature. Methods for detecting such deposition are known in the art. See, e.g., Crowson et al. (2002), supra.

In addition, as described in the working examples, Degos' disease can be associated with prominent vascular C5b-9 MAC deposition as well as elevated serum C reactive protein and factor VIII levels. Methods for detecting each of these parameters are exemplified herein.

In some embodiments, the composition can be administered to a subject prophylactically to prevent the progression of the benign form of Degos' disease to the systemic, multiorgan form of the disease. For example, a subject who has a cutaneous form of Degos' disease can be administered a composition described herein to prevent or lessen the likelihood of development in the patient of the lethal, systemic form of Degos' disease. Similarly, a subject who has a Degos' disease-associated B19 parvoviral infection, an HIV infection, or an autoimmune disease can be administered a composition described herein to prevent or lessen the likelihood of the development of Degos' disease in the patient.

The term "preventing" is art-recognized, and when used in relation to a condition, is well understood in the art, and includes administration of a composition which reduces the frequency of, or delays the onset of, symptoms of a medical condition in a subject relative to a subject which does not receive the composition. Thus, prevention of Degos' disease includes, for example, slowing the progression of the benign form of Degos' disease to the systemic, multiorgan form of the disease in a population of patients receiving a prophylactic treatment relative to an untreated control population, and/or reducing the severity and/or delaying the onset of the one or more symptoms of the disease in a treated population versus an untreated control population, e.g., by a statistically and/or clinically significant amount.

In some embodiments, the inhibitor of human complement (e.g., an anti-C5 antibody or antigen-binding fragment thereof) and/or the inhibitor of interferon alpha can be administered to a subject as a monotherapy. Alternatively, as described above, the inhibitor can be administered to a subject as a combination therapy with another treatment, e.g., another treatment for Degos' disease. For example, the combination therapy can include administering to the subject (e.g., a human patient) one or more additional agents (e.g., anti-coagulants or anti-inflammatory agents) that provide a therapeutic benefit to the subject who has, or is at risk of developing, Degos disease. In some embodiments, the inhibitor of human complement (e.g., an anti-C5 antibody) or inhibitor of interferon alpha and the one or more additional active agents are administered at the same time. In other embodiments, the inhibitor is administered first in time and the one or more additional active agents are administered second in time. In some embodiments, the one or more additional active agents are administered first in time and the inhibitor is administered second in time.

The inhibitor of human complement or inhibitor of interferon alpha can replace or augment a previously or currently administered therapy. For example, upon treating with an anti-C5 antibody or antigen-binding fragment thereof, administration of the one or more additional active agents can cease or diminish, e.g., be administered at lower levels. In some embodiments, administration of the previous therapy can be maintained. In some embodiments, a previous therapy will be maintained until the level of inhibitor of human complement (e.g., an anti-C5 antibody) or inhibitor of interferon alpha reaches a level sufficient to provide a therapeutic effect. The two therapies can be administered in combination.

Monitoring a subject (e.g., a human patient) for an improvement in Degos' disease, as defined herein, means evaluating the subject for a change in a disease parameter, e.g., an improvement in one or more symptoms of the disease. For example, a medical practitioner can examine the extent of vascular C5b-9 MAC deposition before and after treatment using a complement inhibitor described herein. Such symptoms include any of the symptoms of Degos' disease described herein. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for Degos' disease described herein.

Ex Vivo Approaches.

Where the inhibitor of human complement or inhibitor of interferon alpha is a polypeptide (e.g., an antibody) or a nucleic acid (e.g., an siRNA or anti-sense nucleic acid), an ex vivo strategy for treating or preventing Degos disease can involve transfecting or transducing one or more cells obtained from a subject with a polynucleotide encoding the protein or nucleic acid. For example, the cells can be transfected with a single vector encoding a heavy and light chain of an anti-C5 antibody or the cells can be transfected with a first vector encoding a heavy chain and a second vector encoding a light chain of the antibody.

The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells can act as a source (e.g., sustained or periodic source) of the complement inhibitor (e.g., the anti-C5 antibody or antigen-binding fragment thereof, or anti-C5 siRNA) or inhibitor of interferon alpha for as long as they survive in the subject. In some embodiments, the vectors and/or cells can be configured for inducible or repressible expression of the antibody (see, e.g., Schockett et al. (1996) *Proc Natl Acad Sci USA* 93: 5173-5176 and U.S. Pat. No. 7,056,897.)

Preferably, the cells are obtained from the subject (autologous), but can potentially be obtained from a subject of the same species other than the subject (allogeneic).

Suitable methods for obtaining cells from a subject and transducing or transfecting the cells are known in the art of molecular biology. For example, the transduction step can be accomplished by any standard means used for ex vivo gene therapy, including calcium phosphate, lipofection, electroporation, viral infection (see above), and biolistic gene transfer. See, e.g., Sambrook et al. (supra) and Ausubel et al. (1992) "Current Protocols in Molecular Biology," Greene Publishing Associates. Alternatively, liposomes or polymeric microparticles can be used. Cells that have been successfully transduced can be selected, for example, for expression of the coding sequence or of a drug resistance gene.

Kits

The disclosure also features articles of manufacture or kits, which include a container with a label; and a composition containing one or more (e.g., one, two, three, four, five, six, seven, eight, nine, or 10 or more) inhibitor(s) of human complement (e.g., an anti-C5 antibody or antigen-binding fragment thereof) and/or one or more (e.g., one, two, three, four, five, six, seven, eight, nine, or 10 or more) inhibitors of interferon alpha (e.g., an anti-interferon alpha antibody). The label indicates that the composition is to be administered to a subject (e.g., a human) having, suspected of having, or at risk for developing, Degos' disease. The kit can, optionally, include a means for administering the composition to the subject. For example, the kits can include one or more syringes.

In some embodiments, the kits can contain two or more (e.g., three, four, five, six, seven, eight, nine, or 10 or more) different types of inhibitors of human complement. For example, a kit can contain an anti-C5 antibody (or antigen-binding fragment thereof) and a siRNA that binds to an mRNA that encodes a human C5 protein. In some embodiments, the kit can contain an anti-C5 antibody, a siRNA, and a small molecule inhibitor of complement.

In some embodiments, the kits can further include one or more additional active agents such as any of those described herein. For example, the kits can include one or more anticoagulants, anti-thrombotic agents, or anti-inflammatory agents. The kits can also include one or more B cell-targeted therapies such as an anti-CD20 antibody. The kits can optionally include one or more means for detecting the presence of anti-cardiolipin antibodies, the lupus anticoagulant, antiphospholipid antibodies, and/or vascular IgA deposition.

The following examples are intended to illustrate, not limit, the invention.

EXAMPLES

Example 1

Materials and Methods

Routine Light Microscopy.

Five-micron thick sections of paraffin embedded, formalin fixed tissue were stained with hematoxylin and eosin and examined by conventional light microscopy.

Immunohistochemical assessment for MxA. The slides for use in detecting MxA protein were placed in Tissue Tek Slide Holders and staining dishes (Miles, Elkhart, IL) and submersed in 200 mL of EDTA buffer, pH 8.0 (Zymed Laboratories, South San Francisco, CA). Following a 30-minute incubation with the primary antibodies, staining was performed using the commercially available Vision BioSystems Define Kit adhering to the protocol. Incubation with the primary antibodies was conducted using the following dilutions: anti-MxA antibody 1:1600. A semi-qualitative assessment was made in regards to the extent of staining based on an approximate percentage of cells stained for a particular marker as well as the distribution of staining across the slide. Slides were cover-slipped using the Shandon™ Consul-Mount™ Histology (Product No. 9990440) system on a Consul™ automated cover-slipper (ThermoShandon, Pittsburgh, PA). See Magro et al. (2009)*J Cutan Pathol* (November 4, electronic publication ahead of print; PMID: 19891658).

Immunofluorescence Studies on Tissue.

The following immunofluorescence studies (as described in Crowson and Magro (1996) *Human Pathol* 27:15-19) were performed on skin biopsy material obtained in Michael's transport medium and subsequently stored at −30° C. Direct immunofluorescence (DIF) studies for immunoglobulin G (IgG), IgA, IgM, fibrin, and complement component C3 (DAKO, Carpinteria, Calif., USA) were performed on lesional skin by the overlay of fluorescein-conjugated primary antibodies upon individual biopsy sections. An indirect immunofluorescence (IF) methodology with a fluorescein-conjugated rabbit anti-mouse antibody was used to detect the presence of C5b-9 MAC (DAKO), by way of its binding to a primary anti-C5b-9 antibody initially contacted to a biopsy section.

Electron Microscopy.

Skin biopsy tissue was placed in glutaraldehyde fixative for ultrastructural examination.

Cell Culture for Indirect Immunofluorescence and Western Blot Studies.

Neonatal human dermal blood microvascular endothelial cells, HMVEC-dBlNeo (Lonza, Walkersville, Md.), were cultured at 37° C. in complete medium (EGM®-2 Basal Medium supplemented with EGM®-2 MV BulletKit® reagents and 5% Premium FBS) (Lonza) with 5% $CO_2$. The cells were cultured for a time sufficient to reach 75% to 80% confluency in the culture flasks. The cells were then washed with warm phosphate-buffered saline (PBS) and harvested using a 1× trypsin-EDTA solution (Sigma-Aldrich, St. Louis, Mo.). After an additional wash with PBS, the cells were re-plated in pre-warmed complete medium onto tissue culture chamber slides (Nunc Lab-Tek™ Chamber Slide System, 2 wells on Permanox™, Sigma-Aldrich) at a density of $2 \times 10^4$ cells/mL. The chamber slides were cultured for 24 hours at 37° C. with 5% $CO_2$ after which time the media was discarded. Following removal of the media, the slides of each chamber were removed, rinsed in PBS, and then air dried in combination with paper towels to wick away excess PBS. The dried slides were then stored at −80° C. in an airtight container until examined using immunofluorescence microscopy.

Western blot studies. The cultured HMVEC-dBlNeo cells were lysed using a lysis buffer consisting of 0.05M sodium fluoride, 1% Triton X-100, 50mM Tris-HC1 (pH 8.0), 150mM NaC1, 1mM sodium orthovanadate, 1mM phenylmethylsulfonyl fluoride, and a 1:200 dilution of Calbiochem Protease Inhibitor Cocktail Set III (EMD Chemicals, Inc., Gibbstown, NJ) for 30 minutes at 4° C. with occasional vortexing. The lysates were then cleared of nuclei and other insoluble material by microcentrifugation. Next, sodium dodecyl sulfate-polyacrylamide gel (SDS-PAGE) loading buffer containing β-mercaptoethanol (5% final concentration) was added to the cell lysate (1:4 dilution of the 5X loading buffer into lysate) prior to boiling for two minutes. Lysates were then resolved by electrophoresis through an 8% to 16% gradient Tris-HC1 SDS-PAGE gels (Bio-Rad®, Hercules, CA) and transferred to Whatman Protran™ nitrocellulose membranes (Sigma-Aldrich). Membranes were incubated for six hours at room temperature with a blocking solution of 3% non-fat milk in Tris-buffered saline with 0.1% Tween-20 (TBS-T) on an orbital shaker, and then fitted into a Miniblotter 25blotting manifold (Immunetics™, Cambridge, MA). Miniblotter wells were filled with either patient or healthy control serum diluted 1:250 in TBS-T containing 0.2% bovine serum albumin, and the Miniblotter rocked gently overnight at 4° C. on an orbital shaker. The sera were then removed, the wells washed twice with TBS-T, and the membranes removed from the apparatus. Following additional extensive washing with TBS-T, the membranes were stained for two hours at room temperature with a 1:20,000 dilution of horseradish peroxidase-conjugated goat anti-human Ig(heavy and light chain) secondary antibody (SouthernBiotech™, Birmingham, AL). After extensive washing of the membranes with TBS-T, antibody complexes were detected using Supersignal® West Pico Chemiluminescent Substrate (Thermo Scientific®), Rockford, IL), with chemilluminescent bands visualized on HyBlot CL™ autoradiography film (Denville Scientific, Inc., Metuchen, NJ).

Indirect Immunofluorescence Studies to Detect the Presence of Anti-Endothelial Cell Antibodies.

Serum samples were diluted to a dilution factor of 1:100 and incubated with human cutaneous endothelial cells. Antibody binding was detected using a fluorescein-conjugated goat anti-human IgG (diluted 1:100 in PBS; Caltag, Burlingame, Calif.). Fluorescent-antibody complexes were visualized using an Olympus microscope and images were recorded with a digital camera.

Example 2

Results

Clinical History.

Over a two-year period, a 43-year old previously healthy male developed asymptomatic small cutaneous lesions initially defined by raised papular lesions eventuating into depressed white scars. On 23 Jul. 2009, the patient entered the emergency room with a three-day history of intermittent, low grade fevers accompanied by severe abdominal pain and green tinged vomiting. An exploratory laparotomy was performed—a small segment of bowel was removed. Both the skin and bowel specimens showed classic changes associated with Degos' Disease. No anticardiolipin antibodies, anti-beta 2 glycoprotein antibodies, or lupus anticoagulant was detected. Additional laboratory tests confirmed abnormally elevated serum factor VIII levels (199 above normal), elevated von Willebrand factor (VWF) levels (217 above normal), and increased vascular endothelial cell growth factor (VEGF) levels. While the complement component proteins C2, C3 and C4 were determined to be within normal levels, C5 levels were elevated.

A thoracocentesis was performed on the patient to relieve the pneumothorax. The patient was started on intravenous gamma globulin and Lovenox® at 490 mg daily. During a follow up visit on 12 Aug. 2009, the patient had lost 15 pounds due to decreased appetite attributable to persistent abdominal pain. A respiratory exam of the patient demonstrated decreased breath sounds in the bibasilar regions. The patient's C reactive protein, VWF, and VEGF levels remained elevated at 6.51, 177, and 971, respectively. After four treatments of IVIG there was some improvement in the patient's skin lesions, although the patient continued to suffer from abdominal pain. In October 2009, the patient developed chest pain and shortness of breath, which necessitated hospital admission. The patient quickly decompensated hemodynamically and was placed in the medical intensive care unit. The patient was noted to have an ejection fraction of 14% associated with a large pericardial and pleural effusion. A pericardial biopsy was obtained that confirmed a severe thrombotic microangiopathy consistent with Degos' disease. Vascular C5b-9 deposition was also observed. Eculizumab was then administered to the patient. An almost immediate improvement in the patient's condition occurred. For example, the patient's ejection fraction improved dramatically. Within 24 hours of receiving the eculizumab, the patient was extubated and transferred to the medical ward. Over the next several weeks, the patient was symptomatically better and there was an objective improvement in the appearance of his skin lesions.

Pathology.

Three sets of skin biopsies were obtained from the patient. The time at which these biopsies were performed was temporally associated with variations in treatment intervention. The first set was obtained from the patient prior to the administration of either IVIG or eculizumab to the patient and included two evolutionary phases of his skin lesions. One biopsy was from a raised papular lesion revealing striking mesenchymal mucin deposition, a morphologic finding that led to an initial erroneous diagnosis of tumid lupus erythematosus two years previously. Examination of the vasculature revealed abnormalities including endothelial cell swelling, necrosis, and detachment with focal mural and luminal fibrin deposition. A biopsy of the classic Degos' disease associated porcelain depressed scarred papule demonstrated prominent epidermal thinning and dermal fibrosis with vascular drop out. The vessels demonstrated an extensive occlusive thrombotic microangiopathy with endothelial cell degeneration/necrosis and endothelial cell sloughing into the vascular lumen. All of the biopsies revealed a dearth of inflammatory cells. The bowel specimen showed an extensive obliterative vasculopathy affecting larger caliber arteries of the submucosa.

Several weeks after commencing IVIG, another skin biopsy was obtained, analysis of which revealed persistent cutaneous ischemic changes including mucin, fibrosis and epithelial thinning. However, there was a reduction in the extent of active vascular injury. Vessels containing significant luminal and mural fibrin deposition were not observed.

An additional set of biopsies (the third set) was obtained from the patient two weeks after administration of eculizumab. Analysis of the biopsied tissue revealed superficial fibroplasias with vascular drop out. The vessels were thickened reflecting basement membrane zone reduplication. Only rare vessels exhibited endothelial cell damage and thrombosis.

Interferon Alpha Assessment in Tissue Samples.

There was extensive expression of MxA protein in endothelial cells, inflammatory cells, and epidermal keratinocytes.

C5b-9 Immunofluorescence Studies.

Indirect immunofluorescence studies revealed extensive deposits of C5b-9 within the cutaneous vasculature of the first set of biopsies prior to commencing IVIG and or eculizumab. The deposition pattern was both intraluminal and mural. The extent of deposition was very prominent involving several vessels throughout the dermis. Although IVIG reduced C5b-9 deposition to some degree, the extent of C5b-9 deposition observed in biopsies obtained from the patient following eculizumab therapy was markedly diminished. Only three vessels showed mural C5b-9 deposition.

Electron Microscopy.

Ultrastructural analysis of the biopsied tissue obtained pretreatment showed extensive tubular reticular structures in the epidermal keratinocytes and in endothelial cells throughout the dermis. The lining endothelial cells showed profound degenerative changes with detachment of the cells from the vessel lumens. The vascular basement membrane zones were reduplicated and also showed by collagen deposition.

Antiendothelial Cell Antibody Assay.

Patient serum obtained prior to eculizumab treatment and serum obtained two weeks following eculizumab treatment were incubated with cutaneous endothelial cells and fluorescein-conjugated human anti-IgG antibodies. A granular nuclear decoration was observed in most of the endothelial cells in the pre- and post-eculizumab treatment samples. No staining was observed when the patient serum was contacted to human umbilical vein endothelial cells.

Western Blot Studies Using Endothelial Cell Lysates.

The pre- and post-treatment patient serum was also used in a Western blot analysis to identify the protein or proteins to which the human-anti-human antibodies in the patient serum bind. As described above, the pre- and post-treatment serum was incubated with a membrane containing the size-resolved endothelial cell proteins and any binding of antibodies to the proteins of the membrane was detected by way of a fluorescein-conjugated secondary antibody. A distinct band of immunoreactivity corresponding to a molecular weight of 92 kDa was observed. A similar band of reactivity was not identified in normal control cases or in Western blots of lysates of human umbilical vein endothelial cells.

Assessment of Serum Interferon Alpha Levels.

Interferon alpha levels in the peripheral blood of the patient were very high—measuring 20.56, which was comparable to patients having lupus erythematosus and several fold higher than interferon alpha levels in blood from healthy patients.

Discussion.

The patient described herein developed multifocal intestinal, pericardial, myocardial and cutaneous ischemia, attributable to prominent endothelial cell injury. The patient's symptoms were consistent with Degos' Disease. Using cutaneous endothelial cells as substrate, there was evidence of anti-endothelial cell antibodies using indirect immunofluorescence and Western blot techniques. A dominant antigenic epitope was isolated based on Western Blot analysis, although its identity is unclear. In view of the finding that the anti-endothelial cell antibodies were not reactive with human umbilical vein cells, it is likely that the antiendothelial cell antibodies observed in this patient were organ selective, whereby the immunogenicity to the selected endothelial cell based epitope is site dependent.

The studies described herein implicate complement-mediated endothelial injury as the likely effector mechanism in the Degos' disease patient treated with eculizumab. There was a dramatic objective clinical and pathological response to the administration of the drug.

Interferon alpha expression was markedly increased in the patient's serum as well as within his tissue. Interferon alpha is known to upregulate adaptive and innate immunity, potentiating the effects of any antigenic trigger. The administration of exogenous interferon alpha has been reported as a cause of cutaneous thrombosis and ulceration. The patient's interferon alpha signature in the peripheral blood was remarkably similar to that observed in patients with SLE although he had no specific clinical features of systemic lupus erythematosus. The findings described herein support a conclusion that inhibition of interferon alpha in patients with Degos' disease can be useful for treating the disease.

In conclusion, eculizumab defines an important therapeutic modality to treat Degos' disease that is otherwise fatal. The exact trigger to the activation of the complement cascade sequence is unclear. While anti-endothelial cell antibodies (e.g., autoantibodies that bind to a 92 kDa antigen present on endothelial cells) provoking activation of the classic complement cascade sequence may be causative of C5b-9 deposition, the role of epitope spreading in the natural course of tissue injury precludes establishing a direct causal effect of these antibodies. Nonetheless at some point in the patient's clinical course additional B cell targeted therapies to reduce the production of these antibodies would be useful for the treatment of Degos' disease provided that the autoantibodies persist.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for treating a patient afflicted with Degos' disease, the method comprising administering an antibody, or antigen-binding fragment thereof, that binds to a human complement component C5 protein, to a patient afflicted with Degos' disease, in an amount sufficient to treat the disease or lessen the severity of one or more symptoms of the disease, wherein the Degos' disease is multiorgan, systemic Degos' disease and wherein the one or more symptoms is selected from the group consisting of skin lesions, gastrointestinal bleeding, vomiting, enterocutaneous fistula, facial and acral paraesthesia, headaches, dizziness, aphagia, paraplegia, gaze palsy, epilepsy, memory loss, altered sensation, strokes, diplopia, ptosis, visual-field defects, weakness, shortness of breath, and chest pain.

2. The method of claim 1, wherein the antibody, or antigen-binding fragment thereof, is chronically administered to the patient.

3. The method of claim 1, wherein the Degos' disease is associated with a B19 parvoviral infection or human immunodeficiency virus infection.

4. The method of claim 1, wherein the Degos' disease is idiopathic.

5. The method of claim 1, wherein the Degos' disease pathologically affects the gastrointestinal tract, the central nervous system, or the cardiovascular system.

6. The method of claim 1, wherein the Degos' disease is refractory to at least one therapy selected from the group consisting of an anti-inflammatory agent, an anticoagulant, an antithrombotic, and intravenous immunoglobulin.

7. The method of claim 1, wherein the antibody, or antigen or antigen binding fragment thereof, inhibits the cleavage of complement component C5 into fragments C5a and C5b.

8. The method of claim 1, wherein the antibody, or antigen-binding fragment thereof, is selected from the group consisting of a humanized antibody, a recombinant antibody, a diabody, a chimerized or chimeric antibody, a deimmunized human antibody, a fully human antibody, a single chain antibody, an Fv fragment, an Fd fragment, an Fab fragment, an Fab' fragment, and an F(ab')₂ fragment.

9. The method of claim 1, wherein the antibody is eculizumab.

10. The method of claim 1, wherein the antibody is pexelizumab.

11. The method of claim 1, further comprising administering to the patient an inhibitor of interferon alpha.

12. The method of claim 11, wherein the inhibitor of interferon alpha is an antibody, or an antigen-binding fragment thereof, that binds to interferon alpha or an interferon alpha receptor.

13. A method for treating a patient afflicted with Degos' disease, the method comprising administering eculizumab to a patient afflicted with Degos' disease, in an amount sufficient to treat the disease or lessen the severity of one or more symptoms of the disease, wherein the Degos' disease is multiorgan, systemic Degos' disease and wherein the one or more symptoms is selected from the group consisting of skin lesions, gastrointestinal bleeding, vomiting, enterocutaneous fistula, facial and acral paraesthesia, headaches, dizziness, aphagia, paraplegia, gaze palsy, epilepsy, memory loss, altered sensation, strokes, diplopia, ptosis, visual-field defects, weakness, shortness of breath, and chest pain.

14. A method for treating a patient afflicted with Degos' disease, the method comprising administering pexelizumab to a patient afflicted with Degos' disease, in an amount sufficient to treat the disease or lessen the severity of one or more symptoms of the disease, wherein the Degos' disease is multiorgan, systemic Degos' disease and wherein the one or more symptoms is selected from the group consisting of skin lesions, gastrointestinal bleeding, vomiting, enterocutaneous fistula, facial and acral paraesthesia, headaches, dizziness, aphagia, paraplegia, gaze palsy, epilepsy, memory loss, altered sensation, strokes, diplopia, ptosis, visual-field defects, weakness, shortness of breath, and chest pain.

15. A method for treating a patient afflicted with Degos' disease, the method comprising administering a complement inhibitor to a patient afflicted with Degos' disease, in an amount sufficient to treat the disease or lessen the severity of one or more symptoms of the disease, wherein the Degos' disease is multiorgan, systemic Degos' disease, wherein the one or more symptoms is selected from the group consisting of skin lesions, gastrointestinal bleeding, vomiting, enterocutaneous fistula, facial and acral paraesthesia, headaches, dizziness, aphagia, paraplegia, gaze palsy, epilepsy, memory loss, altered sensation, strokes, diplopia, ptosis, visual-field defects, weakness, shortness of breath, and chest pain, and wherein the complement inhibitor is selected from the group consisting of soluble CR1, LEX-CR1, MCP, DAF, CD59, Factor H, cobra venom factor, FUT-175, complestatin, and K76 COOH.

16. The method of claim 13, wherein eculizumab is chronically administered to the patient.

17. The method of claim 14, wherein pexelizumab is chronically administered to the patient.

18. The method of claim 15, wherein the complement inhibitor is chronically administered to the patient.

* * * * *